(12) United States Patent
Green et al.

(10) Patent No.: US 7,268,136 B2
(45) Date of Patent: Sep. 11, 2007

(54) COMPOSITIONS USEFUL AS INHIBITORS OF PROTEIN KINASES

(75) Inventors: Jeremy Green, Burlinton, MA (US); Ronald Grey, Jr., Cambridge, MA (US); Albert C. Pierce, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 97 days.

(21) Appl. No.: 10/738,956

(22) Filed: Dec. 17, 2003

(65) Prior Publication Data

US 2004/0192696 A1 Sep. 30, 2004

Related U.S. Application Data

(60) Provisional application No. 60/435,124, filed on Dec. 18, 2002.

(51) Int. Cl.
*C07D 487/04* (2006.01)
*A61K 31/5025* (2006.01)
*A61P 35/02* (2006.01)

(52) U.S. Cl. .................... 514/248; 544/118; 544/236; 514/233.2

(58) Field of Classification Search ............... 544/118, 544/236; 514/233.2, 248
See application file for complete search history.

(56) References Cited

U.S. PATENT DOCUMENTS

| 3,948,912 A | * | 4/1976 | Berger et al. | ............... 544/236 |
| 6,255,305 B1 | | 7/2001 | Broughton et al. | ......... 514/248 |

FOREIGN PATENT DOCUMENTS

| DE | 2 215 999 | 10/1973 |
| DE | 2 254 783 | 5/1974 |
| DE | 2254783 A * | 5/1974 |
| DE | 2 261 693 | 6/1974 |
| DE | 2 261 735 | 6/1974 |
| DE | 100 38 019 A1 | 2/2002 |
| WO | WO99/67245 | 12/1999 |
| WO | WO 02/083139 | 10/2002 |
| WO | WO 02/083675 | 10/2002 |
| WO | WO 03/074525 | 9/2003 |

OTHER PUBLICATIONS

Francavilla et al. Journal of Heterocyclic Chemistry (1971), 8(3), 415-419.*
Pollack et al. Tetrahedron 1966, vol. 22, pp. 2073-2079.*
Legraverend et al. Journal of Heterocyclic Chemistry (1981), 18(5), 893-898.*
STN search printout (4 pages).*
Bratušk et al., "Synthesis and Reactivity of (Z)-3-benzoylamino-4-dimethylamino-2-oxo-3-butene. Preparation of 1-aryl- and 1-heteroaryl-substituted 4-benzoylamino-5-methyl-1*H*-pyrazoles", Heterocycles, vol. 57, No. 11, pp. 2045-2064, (2002).
Bratušk et al., "Transformation of 4-(1-Dimethylaminoethylidene)-2-phenyl-5(4*H*)-oxazolone into Methyl 2-Benzoylamino-3-oxobutanoate. The Synthesis of 1-Substituted 4-Benzoylamino-3-methyl-5(2H)-pyrazolones", J. Het. Chem., vol. 35, pp. 1281-1284, (1998).
Parravicini, et al., "Derivati Della 3-idrazinopiridazina", Nota II Farmaco, vol. 34., No. 4, pp. 299-310, (1979).
Vraničar et al., "2*H*-Pyran-2-ones as Synthons for (*E*)-α,β-Didehydroamino Acid Derivatives", Tetrahedron, vol. 55, pp. 271-278, (1999).
Pollak et al., "Synthesis of Pyridazine Derivatives-V[1] Formation of s-Triazolo-(4,3-b)-pyridazines and BIS-s-Triazolo-(4,3-b,3',4'-f)-pyridazines", Tetrahedron, vol. 22, pp. 2073-2079, (1966).
Langof et al., "Pyridazines. LXXV. Some Quaternary and Mesoionic s-Triazolo(4,3-*b*)pyridazines", Croatica Chemica Acta, vol. 47, No. 2, pp. 153-157, (1975).
Pollak et al., "Synthesis of Pyridazine Derivatives XXII. s-Triazolo[4,3-b]pyridazine 5-Oxides", J. Het. Chem., vol. 5, No. 4, pp. 513-516, (1968).
Bregar et al., "Pyridazines, LXXXVI Some Mesoionic Mercaptoazolopyridazines", Z. Naturforsch., vol. 31, pp. 1387-1390, (1976).

* cited by examiner

*Primary Examiner*—Kahsay Habte
(74) *Attorney, Agent, or Firm*—Daniel A. Pearson

(57) ABSTRACT

The present invention provides a compound of formula (I):

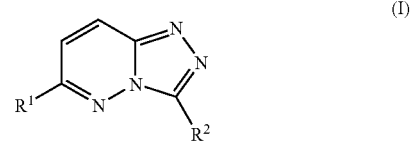

or a pharmaceutically acceptable salt thereof. These compounds are inhibitors of protein kinases, particularly inhibitors of PIM-1, CDK-2, GSK-3, and SRC mammalian protein kinases. The invention also provides pharmaceutically acceptable compositions comprising the compounds of the invention and methods of utilizing those compounds and compositions in the treatment of various protein kinase mediated disorders.

42 Claims, No Drawings

COMPOSITIONS USEFUL AS INHIBITORS OF PROTEIN KINASES

CROSS-REFERENCE TO RELATED APPLICATIONS

The present application claims priority under 35 U.S.C. §119 to U.S. Provisional Application No.: 60/435,124, filed Dec. 18, 2002, entitled "Compositions Useful as Inhibitors of Protein Kinases, the entire contents of which is hereby incorporated by reference.

TECHNICAL FIELD OF THE INVENTION

The present invention relates to inhibitors of protein kinases. The invention also provides pharmaceutical compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif. 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., Cell 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

PIM-1 is the protooncogene activated by murine leukemia virus (Provirus Integration site for Moloney murine leukemia virus) [Cuypers, H. T., et al., Cell 37, 141-150 (1984)]. The expression of the protooncogene produces a non-transmembrane serine/threonine kinase of 313 residues, including a kinase domain consisting of 253 amino acid residues. Two isoforms are known through alternative initiation (p44 and p33) [Saris, C. J. M., et al., *EMBO J.*, 10, 655-664 (1991)]. Two PIM-1 homologs have been described [Baytel, D., Biochim Biophys Acta 1442, 274-85 (1998); Feldman, J., et al., J Biol Chem 273, 16535-16543(1998)]. PIM-2 and PIM-3 are respectively 58% and 69% identical to Pim-1 at the amino acid level. PIM-1 is highly expressed in the liver and spleen during hematopoiesis, and expression is induced by cytokines such as GM-CSF, G-SCF, IL-3, IF-α, and IL-6 [Lilly, M., et al., Oncogene 7, 727-732 (1992); Sato, N., et al., EMBO J. 12, 4181-4189 (1993); Jaster, R., et al., Cell Signal 11, 331-335 (1999); Matikainen, S., et al., Blood 93, 1980-1991 (1999)].

PIM-1 has been implicated in lymphoma development. Induced expression of PIM-1 and the protooncogene c-myc synergize to increase the incidence of lymphomagenesis [Breuer M., et al., Nature 340, 61-63 (1989); van Lohuizen M., et al., Cell 65, 737-52 (1991)]. PIM-1 functions in cytokine signaling pathways and has been shown to play a role in T cell development [Schmidt, T., et al., EMBO J 17, 5349-5359 (1998); Jacobs, H., et al., JEM 190, 1059-1068 (1999)]. Signaling through gp130, a subunit common to receptors of the IL-6 cytokine family, activates the transcription factor STAT3 and can lead to the proliferation of hematopoietic cells [Hirano, T., et al., Oncogene 19, 2548-2556 (2000)]. A kinase-active PIM-1 appears to be essential for the gp130-mediated STAT3 proliferation signal. In cooperation with the c-myc PIM-1 can promote STAT3-mediated cell cycle progression and antiapoptosis [Shirogane, T., et al., Immunity 11, 709-719 (1999)]. PIM-1 also appears to be necessary for IL-3-stimulated growth in bone marrow-derived mast cells [Domen J., et al., Blood 82, 1445-52 (1993)] and survival of FDCP1 cells after IL-3 withdrawal [Lilly, M., et al., Oncogene 18, 4022-4031 (1999)].

Additionally, control of cell proliferation and survival by PIM-1 may be effected by means of its phosphorylation of the well established cell cycle regulators cdc25 [Mochizuki, T., et al., J Biol Chem 274, 18659-18666 (1999)] and/or p21(Cip1/WAF1)[Wang, Z., et al., Biochim Biophys Acta 1593, 45-55 (2002)] or phosphorylation of heterochromatin protein 1, a molecule involved in chromatin structure and transcriptional regulation [Koike N., et al., FEBS Lett 467, 17-21 (2000)].

Cyclin-dependent kinases (CDKs) are serine/threonine protein kinases consisting of a β-sheet rich amino-terminal lobe and a larger carboxy-terminal lobe which is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK-2 Thr160 in order to be fully active [Meijer, L., *Drug Resistance Updates*, 3, 83-88 (2000)].

Each CDK complex is formed from a regulatory cyclin subunit (e.g., cyclin A, B1, B2, D1, D2, D3, and E) and a catalytic kinase subunit (e.g., CDK1, CDK-2, CDK4, CDK5, and CDK6). Each different kinase/cyclin pair functions to regulate the different and specific phases of the cell cycle known as the G1, S, G2, and M phases [Nigg, E., *Nature Reviews*, 2, 21-32 (2001); Flatt, P., Pietenpol, J., *Drug Metabolism Reviews*, 32, 283-305 (2000)].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the overexpression of cyclin D1 is commonly associated with numerous human cancers including breast, colon, hepatocellular carcinomas and gliomas [Flatt, P., Pietenpol, J., *Drug Metabolism Reviews*, 32, 283-305 (2000)]. The CDK-2/cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., *The Cancer Journal*, 6, 192-212 (2000)].

CDKs, especially CDK-2, also play a role in apoptosis and T-cell development. CDK-2 has been identified as a key regulator of thymocyte apoptosis [Williams, O., et al, *European Journal of Immunology*, 709-713 (2000)]. Stimulation of CDK-2 kinase activity is associated with the progression of apoptosis in thymocytes, in response to specific stimuli. Inhibition of CDK-2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegakovirus, herpes virus, and varicella-zoster virus [Meijer, L., *Drug Resistance Updates*, 3, 83-88 (2000)].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, L., *Drug Resistance Updates*, 3, 83-88 (2000)].

Glycogen synthase kinase-3 (GSK-3) is a serine/threonine protein kinase comprised of α and β isoforms that are each encoded by distinct genes [Coghlan et al., *Chemistry & Biology* 2000, 7, 793-803; and Kim and Kimmel, *Curr. Opinion Genetics Dev.*, 2000 10, 508-514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117-130]. These diseases are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455-8459; Cross et al., *Biochem. J.* 1994, 303, 21-26); Cohen, *Biochem. Soc. Trans.* 1993, 21, 555-567; and Massillon et al., *Biochem J.* 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is also associated with Alzheimer's disease. This disease is characterized by the well-known β-amyloid peptide and the formation of intracellular neurofibrillary tangles. Aβ peptides are derived from the amyloid precursor protein (APP) by sequential proteolysis, catalysed by the aspartyl protease BACE2, followed by presenilin-dependent γ-secretase cleavage. It has been demonstrated that antibodies against β-amyloid plaques can slow cognitive decline in patients with Alzheimer's disease (Hock et al., *Neuron*, 2003, 38, 547-554), and thus other β-amyloid-lowering strategies (e.g., the development of agents capable of inhibiting β-amyloid peptide) would be useful in the treatment of Alzherimer's disease and other psychotic and neurodegenerative disorders. Additionally, the neurofibrillary tangles contain hyperphosphorylated Tau protein, in which Tau is phosphorylated on abnormal sites, and thus agents capable of inhibiting the hyperphosphorylation of Tau protein would be useful in the treatment of Alzherimer's disease and other psychotic and neurodegenerative disorders.

GSK-3 is known to phosphorylate these abnormal sites in cell and animal models. Furthermore, inhibition of GSK-3 has been shown to prevent hyperphosphorylation of Tau in cells [Lovestone et al., *Current Biology* 1994, 4, 1077-86; and Brownlees et al., *Neuroreport* 1997, 8, 3251-55]. Therefore, GSK-3 activity promotes generation of the neurofibrillary tangles and the progression of Alzheimer's disease. It has also been shown that GSK-3 facilitates APP processing and that a GSK-3 inhibitor (lithium) inhibits of the generation of Aβ peptides through the inhibition of GSK-3 (Phiel et al. *Nature* 2003, 423, 435-439). Thus, the development of inhibitors of GSK-3 would be useful for the reduction of the formation of amyloid plaques and neurofibrillary tangles, the pathological hallmarks of Alzheimer's Disease, and would also be useful for the treatment of other psychotic and neurodegenerative disorders.

Another substrate of GSK-3 is β-catenin, which is degraded after phosphorylation by GSK-3. Reduced levels of β-catenin have been reported in schizophrenic patients and have also been associated with other diseases related to increase in neuronal cell death [Zhong et al., *Nature* 1998, 395, 698-702; Takashima et al., *PNAS* 1993, 90, 7789-93; and Pei et al., *J. Neuropathol. Exp* 1997,56, 70-78].

GSK-3 activity is also associated with stroke [Wang et al., *Brain Res* 2000, 859, 381-5; Sasaki et al., *Neurol Res* 2001, 23, 588-92; Hashimoto et al., *J. Biol. Chem* 2002, 277, 32985-32991]. Another kinase family of particular interest is the Src family of kinases. These kinases are implicated in cancer, immune system dysfunction and bone remodeling diseases. For general reviews, see Thomas and Brugge, *Annu. Rev. Cell Dev. Biol.* (1997) 13, 513; Lawrence and Niu, *Pharmacol. Ther.* (1998) 77, 81; Tatosyan and Mizenina, *Biochemistry* (Moscow) (2000) 65, 49; Boschelli et al., *Drugs of the Future* 2000, 25(7), 717, (2000).

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 65, 49-58 (2000).

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell*, 69, 551 (1992) and Soriano et al., *Cell*, 64, 693 (1991).

Suppression of arthritic bone destruction has been achieved by the overexpression of CSK in rheumatoid synoviocytes and osteoclasts. Takayanagi et al., *J. Clin. Invest.*, 104, 137 (1999). CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717, (2000).

Src also plays a role in the replication of hepatitis B virus. The virally encoded transcription factor HBx activates Src in a step required for propagation of the virus. Klein et al., *EMBO J.*, 18, 5019, (1999) and Klein et al., *Mol. Cell. Biol.*, 17, 6427 (1997).

A number of studies have linked Src expression to cancers such as colon, breast, hepatic and pancreatic cancer, certain B-cell leukemias and lymphomas. Talamonti et al., *J. Clin. Invest.*, 91, 53 (1993); Lutz et al., *Biochem. Biophys. Res.* 243, 503 (1998); Rosen et al., *J. Biol. Chem.*, 261, 13754 (1986); Bolen et al., *Proc. Natl. Acad. Sci. USA*, 84, 2251 (1987); Masaki et al., *Hepatology*, 27, 1257 (1998); Biscardi et al., *Adv. Cancer Res.*, 76, 61 (1999); Lynch et al., *Leukemia*, 7, 1416 (1993). Furthermore, antisense Src expressed in ovarian and colon tumor cells has been shown to inhibit tumor growth. Wiener et al., *Clin. Cancer Res.*, 5, 2164 (1999); Staley et al., *Cell Growth Diff.*, 8, 269 (1997).

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., *Nature*, 357, 161 (1992). Hck, Fgr and Lyn have been identified as important mediators of integrin signaling in myeloid leukocytes. Lowell et al., *J. Leukoc. Biol.*, 65, 313 (1999). Inhibition of these kinase mediators may therefore be useful for treating inflammation. Boschelli et al., *Drugs of the Future* 2000, 25(7), 717, (2000).

Accordingly, there is a great need to develop inhibitors of PIM-1, CDK-2, SRC, and GSK-3 protein kinases that are useful in treating various diseases or conditions associated with PIM-1, CDK-2, SRC, or GSK-3 activation, particularly given the inadequate treatments currently available for the majority of these disorders.

SUMMARY OF THE INVENTION

It has now been found that compounds of this invention, and pharmaceutically acceptable compositions thereof, are effective as inhibitors of PIM-1, CDK-2, SRC, and GSK-3 protein kinases. In certain other embodiments, these compounds are effective as inhibitors of PIM-1 protein kinase. These compounds have the general formula I:

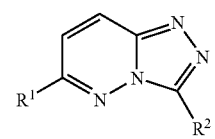

or a pharmaceutically acceptable derivative thereof, wherein $R^1$ and $R^2$ are as defined below.

These compounds and pharmaceutical compositions thereof are useful for treating or preventing a variety of disorders, including, but not limited to, heart disease, diabetes, Alzheimer's disease, immunodeficiency disorders, inflammatory diseases, allergic diseases, autoimmune diseases, destructive bone disorders such as osteoporosis, proliferative disorders, infectious diseases, immunologically-mediated diseases, and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), acute myeloid leukemia (AML), acute promyelocytic leukemia (APL), rheumatoid arthritis, asthma, osteoarthritis, ischemia, cancer, liver disease including hepatic ischemia, heart disease such as myocardial infarction and congestive heart failure, pathologic immune conditions involving T cell activation, and neurodegenerative disorders.

DETAILED DESCRIPTION OF THE INVENTION

1. General Description of Compounds of the Invention

The present invention relates to a compound of formula I:

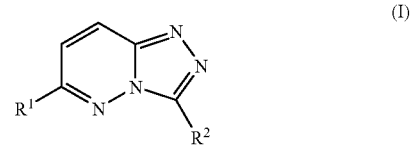

or a pharmaceutically acceptable salt thereof,
wherein $R^1$ is $OR^3$, $SR^3$, or $NR^3R^4$; wherein each occurrence of $R^3$ and $R^4$ is independently $(U)_mR'$, wherein U is an optionally substituted $C_{1-6}$alkylidene chain, wherein up to two methylene units of the chain are optionally and independently replaced by —C(O)—, —C(O)C(O)—, —CONR—, —CONRNR—, —CO$_2$—, —OC(O)—, —NRCO$_2$—, —O—, —NRCONR—, —OC(O)NR—, —NRNR—, —NRCO—, —S—, —SO—, —SO$_2$—, —NR—, —SO$_2$NR—, or —NRSO$_2$—; m is 0 or 1 ; or wherein $R^3$ and $R^4$, taken together with the nitrogen form an optionally substituted 5-8 membered heterocyclyl or heteroaryl ring having 1-3 heteroatoms independently selected from nitrogen, oxygen, or sulfur;

each occurrence of R is independently selected from hydrogen or an optionally substituted $C_{1-6}$ aliphatic group, and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together, or two occurrences of R' on the same substituent or different substituents, taken together, form a 5-8 membered heterocyclyl or heteroaryl ring having 1-3 heteroatoms independently selected from nitrogen, oxygen, or sulfur; and $R^2$ is -(T)$_n$Ar$^1$, wherein T is NR; n is 0 or 1; Ar$^1$ is a 3-7 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur.

In certain embodiments compounds of formula I exclude one or more of, or all of the following compounds:

1) when $R^2$ is optionally substituted 1,3,5-triazine, then $R^1$ is not N-morpholino;

2) when $R^2$ is nitro substituted pyrazolyl, furyl, or thiophene, then $R^1$ is not $NR^3R^4$;

3) when $R^2$ is furyl, then $R^2$ is not $NH_2$;

4) when $R^2$ is optionally substituted pyridyl or phenyl, then $R^1$ is not $OR^3$, where $R^3$ is halogen substituted alkyl;

5) when $R^2$ is phenyl substituted with haloalkyl or haloalkoxy, then $R^1$ is not $NH(C_{1-4}alkyl)$ or $O(CH_2)_2N(Me)_2$;

6) compounds of formula I exclude:
  a. Butanoic acid, 2-(benzylamino)-3[(3-phenyl-1,2,4-triazolo[4,3-b]pyridazin-6-yl)hydrazono]-methyl ester;
  b. Benzamide, N-[2,5-dihydro-3-methyl-5-oxo-1-(3-phenyl-1,2,4-trazolo[4,3-b]pyridazin-6-yl)-1H-pyrazol-4-yl]; and
  c. 2-propenoic acid, 2-(benzylamino)-3-[3,5-dimethyl-1-(3-phenyl-1,2,4-triazolo[4,3-b]pyridazin-6-yl)-1H-pyrazol-4-yl]-;

7) when $R^2$ is phenyl substituted with one or more occurrences of OMe, Me, $NO_2$, Cl, or $CF_3$, then $R^1$ is not optionally substituted morpholino or piperazinyl;

8) when $R^2$ is phenyl or fluoro-substituted phenyl, $R^1$ is not —O—$CH_2$-(triazolyl);

9) when $R^1$ is —NH(cyclopropyl), then $R^2$ is not phenyl substituted with one occurrence of $CF_3$ in the para position;

10) when $R^2$ is unsubstituted phenyl, then $R^1$ is not —$SR^3$, wherein $R^3$ is phenyl substituted with $CF_3$ in the meta position, phenyl substituted with two occurrences of $OCH_3$, $(CH_2)_2OH$, —$(CH_2)COOCH_2CH_3$, or phenyl substituted with one occurrence of Cl in the para position; or 11) when $R^2$ is unsubstituted phenyl, then $R^1$ is not NH(CH)=NOH.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —$R^o$; —$OR^o$; —$SR^o$; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(S)R^o$; —$NR^oC(O)N(R^o)_2$; —$NR^oC(S)N(R^o)_2$; —$NR^oCO_2R^o$; —$NR^oNR^oC(O)R^o$; —$NR^oNR^oC(O)N(R^o)_2$; —$NR^oNR^oCO_2R^o$; —C(O)C(O)$R^o$; —C(O)$CH_2$C(O)$R^o$; —$CO_2R^o$; —C(O)$R^o$; —C(S)$R^o$; —C(O)N($R^o)_2$; —C(S)N($R^o)_2$; —OC(O)N($R^o)_2$; —OC(O)$R^o$; —C(O)N(O$R^o$)$R^o$; —C(NO$R^o$)$R^o$; —S(O)$_2R^o$; —S(O)$_3R^o$; —$SO_2N(R^o)_2$; —S(O)$R^o$; —$NR^oSO_2N(R^o)_2$; —$NR^oSO_2R^o$; —N(O$R^o$)$R^o$; —C(=NH)—N($R^o)_2$; —P(O)$_2R^o$; PO($R^o)_2$; —OPO($R^o)_2$; —$(CH_2)_{0-2}$NHC(O)$R^o$; phenyl (Ph) optionally substituted with $R^o$; —O(Ph) optionally substituted with $R^o$; —$(CH_2)_{1-2}$(Ph), optionally substituted with $R^o$; or —CH=CH(Ph), optionally substituted with $R^o$; wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of $R^o$ are selected from $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2H$, $CO_2$($C_{1-4}$aliphatic), O(halo$C_{1-4}$ aliphatic), or halo $C_{1-4}$aliphatic, wherein each of the foregoing $C_{1-4}$aliphatic groups of $R^o$ is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic group.

Unless otherwise defined above and herein, optional substituents on the nitrogen of a non-aromatic heterocyclic ring are generally selected from —$R^+$, —N($R^+)_2$, —C(O)$R^+$, —$CO_2R^+$, —C(O)C(O)$R^+$, —C(O)$CH_2$C(O)$R^+$, —$SO_2R^+$, —$SO_2N(R^+)_2$, —C(=S)N($R^{+1})_2$, —C(=NH)—N($R^+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of $R^+$ are selected from —$NH_2$, —NH($C_{1-4}$ aliphatic), —N($C_{1-4}$ aliphatic)$_2$, halogen, $C_{1-4}$ aliphatic, —OH, —O($C_{1-4}$ aliphatic), —$NO_2$, —CN, —$CO_2H$, —$CO_2$($C_{1-4}$ aliphatic), —O(halo $C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R+, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of R° (or R+, R, R' or any other variable similarly defined herein), are taken together with the atom(s) to which each variable is bound include, but are not limited to the following: a) two independent occurrences of R° (or R+, R, R' or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R+, R, R' or any other variable similarly defined herein) that are bound to different atoms and are taken together with both of those atoms to form a ring, for example where a phenyl group is substituted with two occurrences of

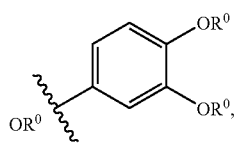

these two occurrences of R° are taken together with the oxygen atoms to which they are bound to form a fused 6-membered oxygen containing ring:

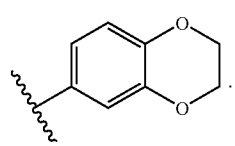

It will be appreciated that a variety of other rings can be formed when two independent occurrences of R° (or R+, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds

As described generally above, in certain embodiments, R$^1$ is NR$^3$R$^4$, OR$^3$, or SR$^3$, and compounds have one of the following general formulas II, III or IV:

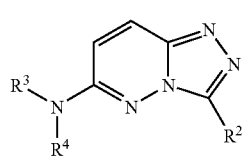

II

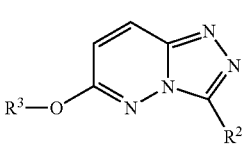

III

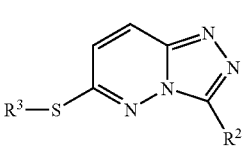

IV

In preferred embodiments, n is 1, T is NR, and R$^2$ is —NRAr$^1$, and compounds have one of the general formulas IIA, IIIA, or IVA:

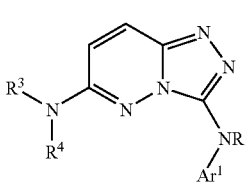

IIA

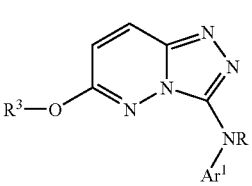

IIIA

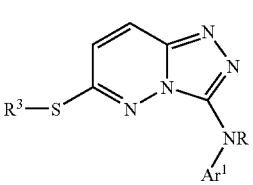

IVA

In certain other preferred embodiments, m is 0, and R² is —Ar¹, and compounds have one of the general formulas IIB, IIIB, or IVB:

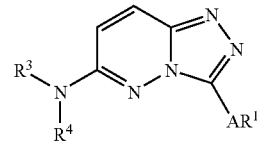

IIB

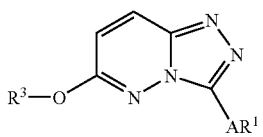

IIIB

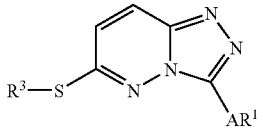

IVB

In certain embodiments, R⁴ is hydrogen or optionally substituted $C_{1-4}$alkyl, and R³ is an optionally substituted aryl, heteroaryl, cycloaliphatic, or heterocycloaliphatic group. In certain other embodiments, R³ is an optionally substituted 5- or 6-membered aryl or heteroaryl group. In yet other embodiments, R³ is an optionally substituted 3-7-membered cycloaliphatic or heterocycloaliphatic group.

In certain embodiments, R⁴ is hydrogen or optionally substituted $C_{1-4}$alkyl, and R³ is an optionally substituted cyclic group selected from:

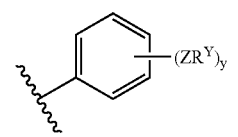

i

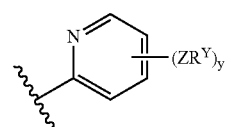

ii

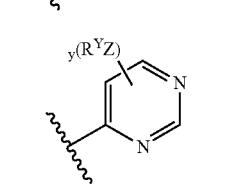

iii

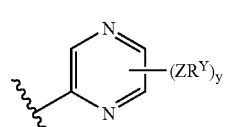

iv

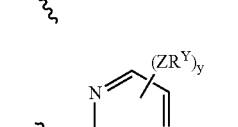

v

-continued

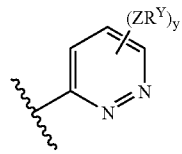

vi

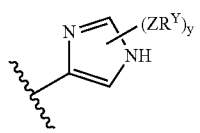

vii

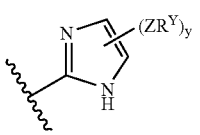

viii

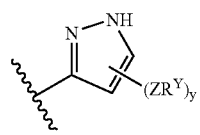

ix

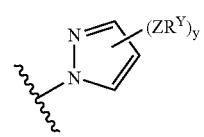

x

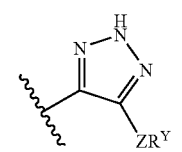

xi

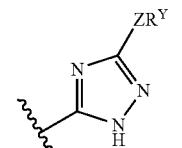

xii

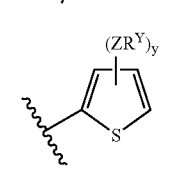

xiii

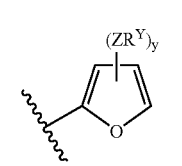

xiv

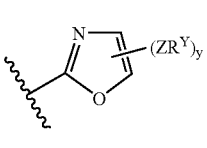

xv

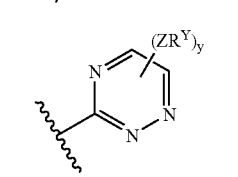

xvi

-continued
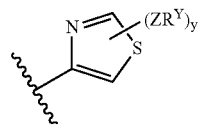 xvii
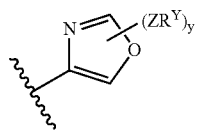 xviii
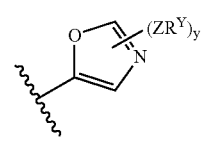 xix
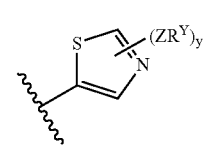 xx
 xxi
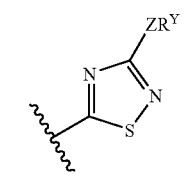 xxii
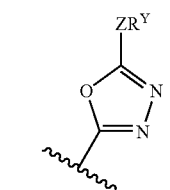 xxiii
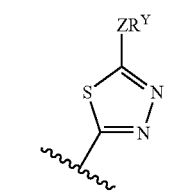 xxiv
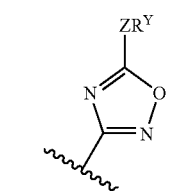 xxv
-continued
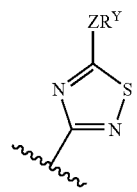 xxvi
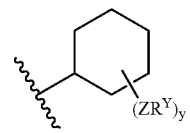 xxvii
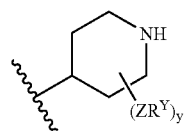 xxviii
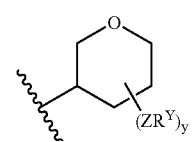 xxix
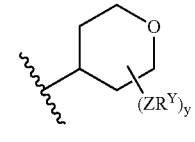 xxx
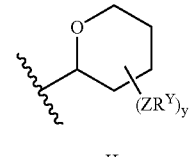 xxxi
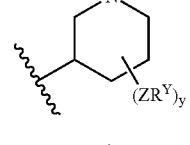 xxxii
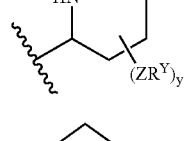 xxxiii
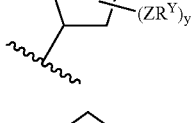 xxxiv
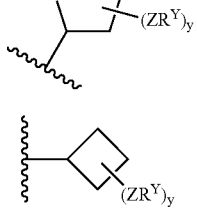 xxxv
xxxvi

xxxvii wherein any substitutable carbon or nitrogen atom is optionally substituted and wherein y is 0-5, Z is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^Y$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, C(O)C(O)R', or $C(O)CH_2C(O)R'$.

In certain other embodiments, $R^3$ and $R^4$, taken together with the nitrogen atom, form a group selected from:

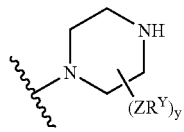

xxxviii

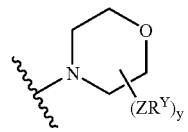

xxxix

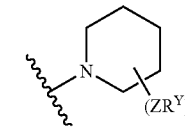

xl

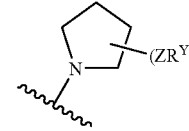

xli

In more preferred embodiments, $R^3$ is selected from one of the following groups:

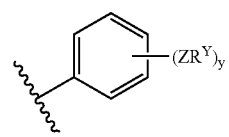

i

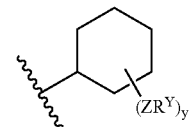

xxvii

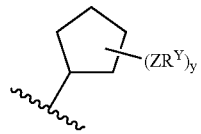

xxxiv

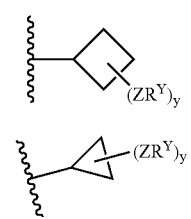

xxxvi xxxvii

In certain preferred embodiments, y is 0-3 and $R^3$ is substituted with 0-3 occurrences of $ZR_Y$. In certain other preferred embodiments, y is 1 or 2. In still other preferred embodiments, y is 0 and $R^3$ is unsubstituted.

In preferred embodiments, each occurrence of $ZR^Y$ is independently halogen, CN, $NO_2$, or an optionally substituted group selected from $C_{1-4}$alkyl, aryl, aralkyl, $—N(R')_2$, $CH_2N(R')_2$, —OR', $CH_2OR'$, —SR', $CH_2SR'$, COOR', or $—S(O)_2N(R')_2$. In more preferred embodiments, each occurrence of $ZR^Y$ is independently Cl, Br, F, CN, $CF_3$, COOH, $—N(CH_3)_2$, —OH, $CH_2OH$, or an optionally substituted group selected from $C_{1-4}$alkoxy, $C_{1-4}$alkyl, phenyl, phenyloxy, benzyl, or benzyloxy. Most preferred $ZR^Y$ groups include those shown below in Table 1.

In still other embodiments, $R^4$ is hydrogen or optionally substituted $C_{1-4}$alkyl, and $R^3$ is $(U)_mR'$, wherein m is 1, and U is an optionally substituted $C_{1-6}$alkylidene chain, wherein up to two methylene units of the chain are optionally and independently replaced by —C(O)—, —C(O)C(O)—, —CONR—, —CONRNR—, —$CO_2$—, —OC(O)—, —$NRCO_2$—, —O—, —NRCONR—, —OC(O)NR'—, —NRNR—, —NRCO—, —S—, —SO—, —$SO_2$—, —NR—, —$SO_2NR$—, or —$NRSO_2$—. In certain preferred embodiments, U is an optionally substituted $C_{1-4}$alkylidene chain, wherein one methylene unit of the chain is optionally replaced by —C(O)—, —CONR—, —$CO_2$—, —OC(O)—, O, or —NRCO—. In more preferred embodiments, U is —$CH_2$(C=O)NH—, —$CH_2$(C=O)O—, —$(CH_2)_2O$—, or —CH=NO—, wherein each occurrence of R' is independently hydrogen or $C_{1-4}$alkyl.

As described generally above, $R^2$ is $(T)_nAr^1$, wherein n is 0 or 1, and T is NR. Preferred $Ar^1$ groups include an optionally substituted cyclic group selected from:

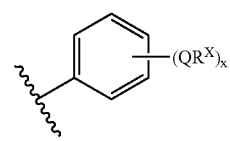

a

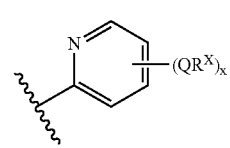

b

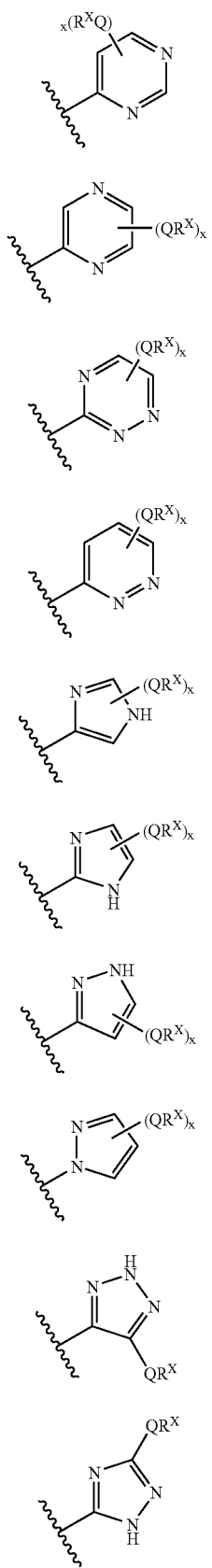
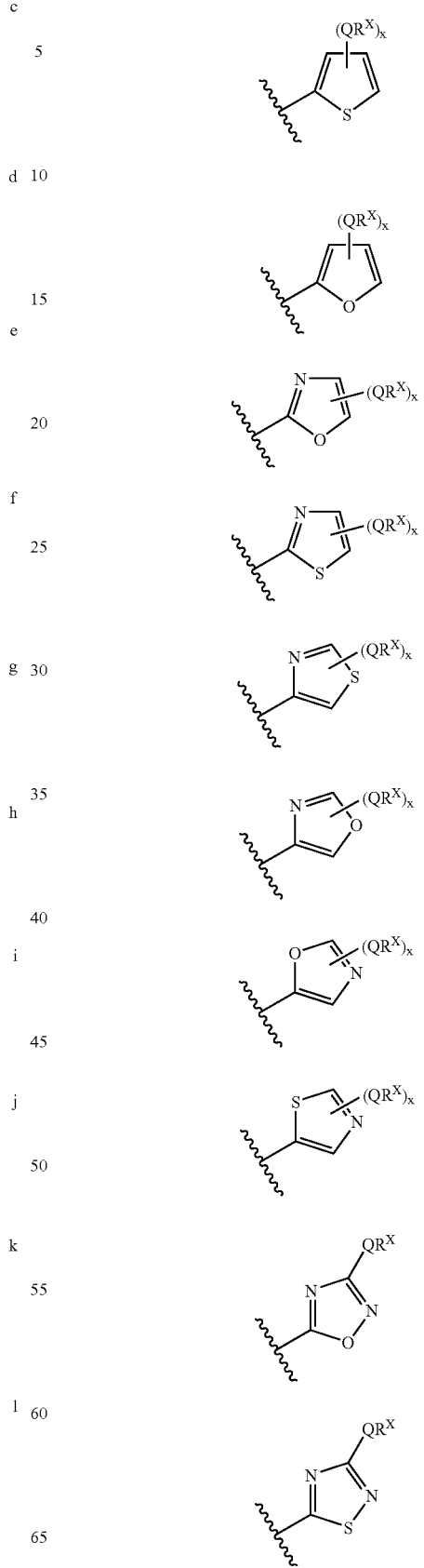

-continued w 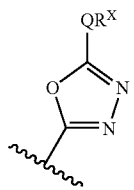

x 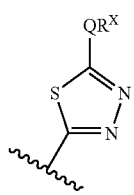

y 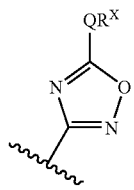

z 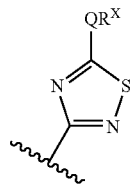

aa 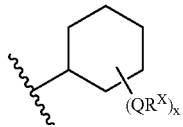

bb 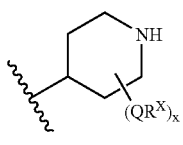

cc 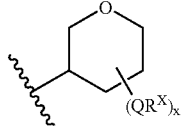

dd 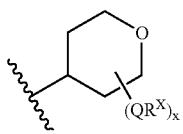

ee 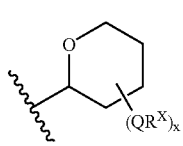

-continued ff 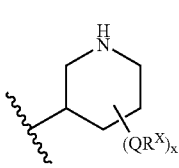

gg 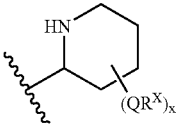

hh 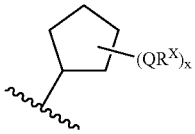

ii 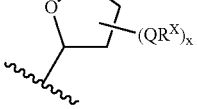

jj 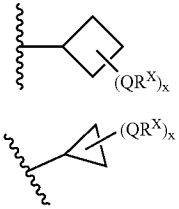

kk 

wherein any substitutable carbon or nitrogen atom is optionally substituted and wherein x is 0-5, Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, C(O)C(O)R', or $C(O)CH_2C(O)R'$.

In certain preferred embodiments, x is 0-3 and $R^2$ is substituted with 0-3 occurrences of $QR^X$. In certain other preferred embodiments, x is 1 or 2. In still other preferred embodiments, x is 0 and $R^2$ is unsubstituted.

In preferred embodiments, each occurrence of $QR^X$ is independently halogen, CN, $NO_2$, or an optionally substituted group selected from $C_{1-4}$alkyl, aryl, aralkyl, —$N(R')_2$, $CH_2N(R')_2$, —OR', $CH_2OR'$, —SR', $CH_2SR'$, COOR', or —$S(O)_2N(R')_2$. In more preferred embodiments, each occurrence of $QR^X$ is independently Cl, Br, F, CN, $CF_3$, COOH, —$N(CH_3)_2$, —OH, $CH_2OH$, or an optionally substituted group selected from $C_{1-4}$alkoxy, $C_{1-4}$alkyl, phenyl, phenyloxy, benzyl, or benzyloxy. Most preferred $QR^X$ groups include those shown below in Table 1.

It will be appreciated that for compounds as described above, certain additional compounds are of special interest. For example, in certain exemplary embodiments, for compounds of general formulas IIA, IIIA, and IVA above, compounds of special interest include those compounds where R⁴ is hydrogen or $C_{1-4}$alkyl; R³ is optionally substituted phenyl; and R² is —NRAr¹, and compounds have one of the following formulas:
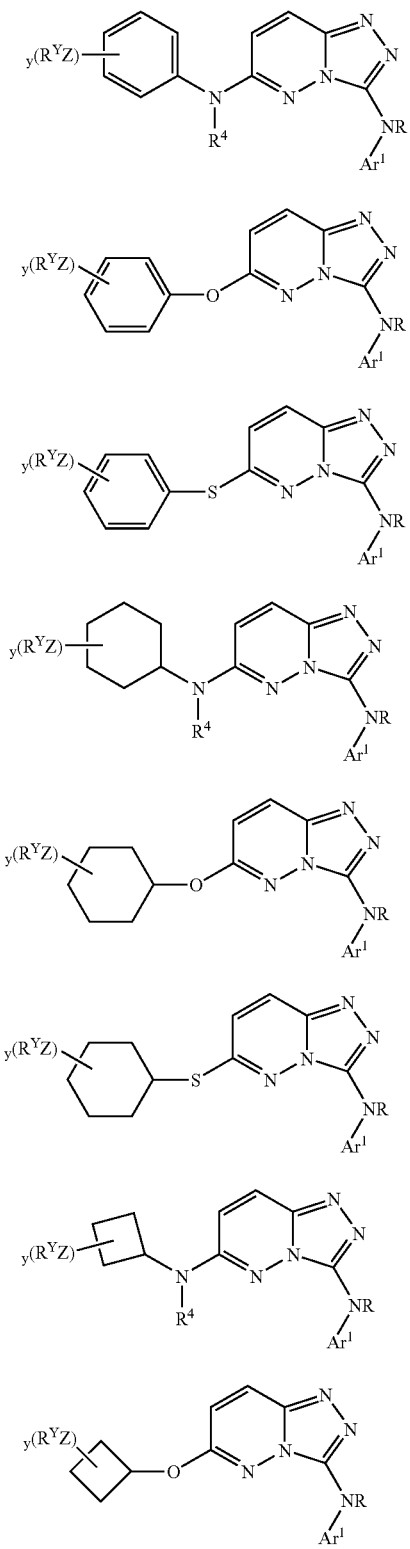
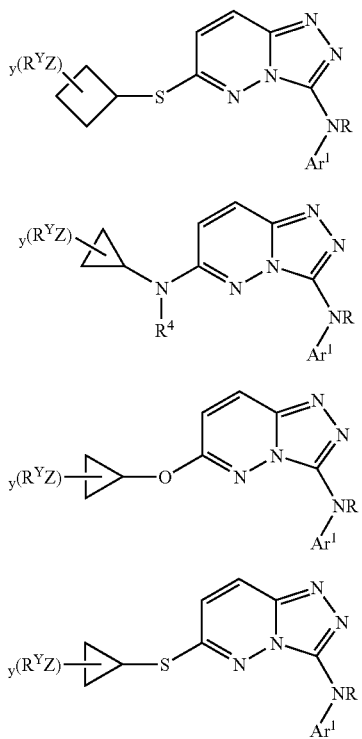
In certain other preferred embodiments, R² is —Ar¹, and compounds have one of the general formulas:
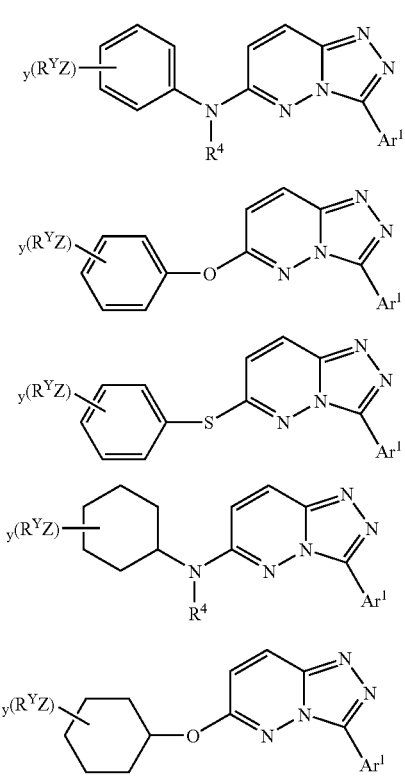

-continued

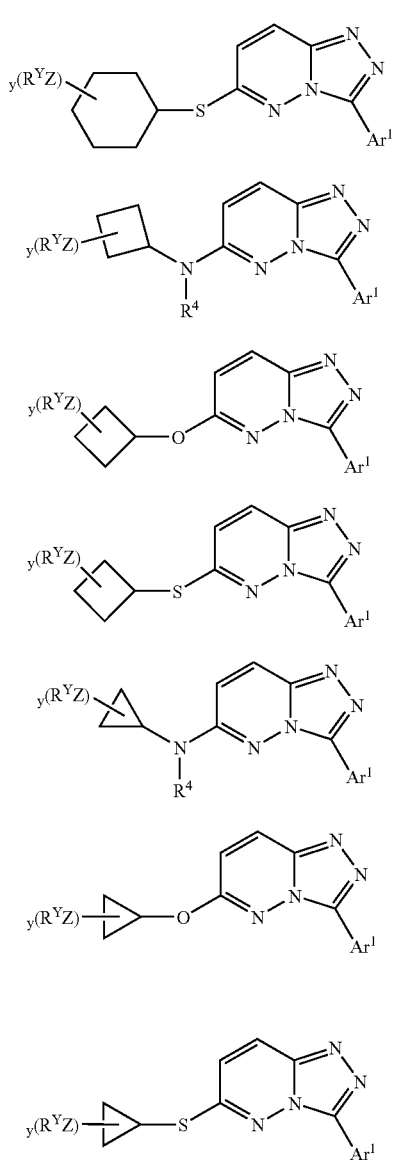

In certain other exemplary embodiments, for compounds of general formulas II, III, and IV above, $R^2$ is $NRAr^1$ and $Ar^1$ is optionally substituted phenyl, and compounds have one of the following formulas:

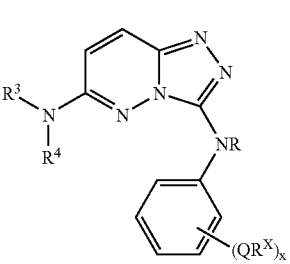

II-A-a

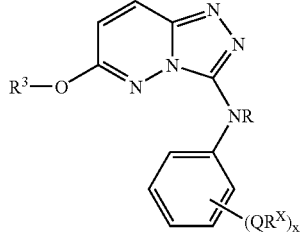

III-A-a

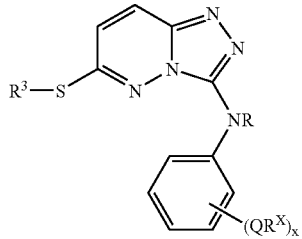

IV-A-a

In certain other preferred embodiments, $R^2$ is $-Ar^1$, wherein $Ar^1$ is optionally substituted phenyl, and compounds have one of the following formulas:

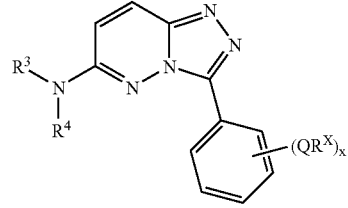

II-B-a

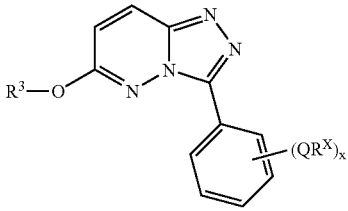

III-B-a

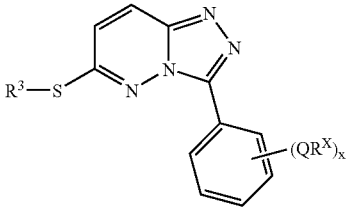

IV-B-a

It will be appreciated that certain subclasses of the foregoing compounds are of particular interest.

For example, in certain preferred embodiments, certain substituents for compounds as described generally for formulas II-A-a, III-A-a, IV-A-a, II-B-a, III-B-a, and IV-B-a above are defined as follows:

a. $R^4$ is hydrogen or $C_{1-4}$alkyl;

b. when n is 1, and T is NR, $R^2$ is hydrogen or $C_{1-4}$alkyl;

c. $R^3$ is a group selected from

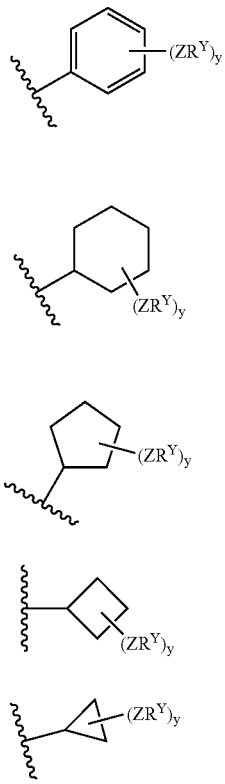

i xxvii xxxiv xxxvi xxxvii wherein y is 0-3, Z is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^Y$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, C(O)C(O)R', or C(O) $CH_2C(O)R'$; and d. x is 0-3, Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, C(O)C(O)R', or $C(O)CH_2C(O)R'$.

In certain preferred embodiments, for compounds described directly above, y is 0-3 and $R^3$ is substituted with 0-3 occurrences of $ZR^Y$. In certain other preferred embodiments, y is 1 or 2. In still other preferred embodiments, y is 0 and $R^3$ is unsubstituted.

In preferred embodiments, each occurrence of $ZR^Y$ is independently halogen, CN, $NO_2$, or an optionally substituted group selected from $C_{1-4}$alkyl, aryl, aralkyl, —$N(R')_2$, $CH_2N(R')_2$, —OR', $CH_2OR'$, —SR', $CH_2SR'$, COOR', or —$S(O)_2N(R')_2$. In more preferred embodiments, each occurrence of $ZR^Y$ is independently Cl, Br, F, CN, $CF_3$, COOH, —$N(CH_3)_2$, —OH, $CH_2OH$, or an optionally substituted group selected from $C_{1-4}$alkoxy, $C_{1-4}$alkyl, phenyl, phenyloxy, benzyl, or benzyloxy. Most preferred $ZR^Y$ groups include those shown below in Table 1.

In certain preferred embodiments for compounds described directly above, x is 0-3 and $R^2$ is substituted with 0-3 occurrences of $QR^X$. In certain other preferred embodiments, x is 1 or 2. In still other preferred embodiments, x is 0 and $R^2$ is unsubstituted.

In preferred embodiments, each occurrence of $QR^X$ is independently halogen, CN, $NO_2$, or an optionally substituted group selected from $C_{1-4}$alkyl, aryl, aralkyl, —$N(R')_2$, $CH_2N(R')_2$, —OR', $CH_2OR'$, —SR', $CH_2SR'$, COOR', or —$S(O)_2N(R')_2$. In more preferred embodiments, each occurrence of $QR^X$ is independently Cl, Br, F, CN, $CF_3$, COOH, —$N(CH_3)_2$, —OH, $CH_2OH$, or an optionally substituted group selected from $C_{1-4}$alkoxy, $C_{1-4}$alkyl, phenyl, phenyloxy, benzyl, or benzyloxy. Most preferred $QR^X$ groups include those shown below in Table 1.

In still other exemplary embodiments, for compounds of general formulas II, III, or IV, $R^3$ is an optionally substituted group selected from phenyl, cyclohexyl, cyclobutyl or cyclopropyl, and $R^2$ is $NRAr^1$, wherein $Ar^1$ is optionally substituted phenyl, and compounds have one of the following formulas:

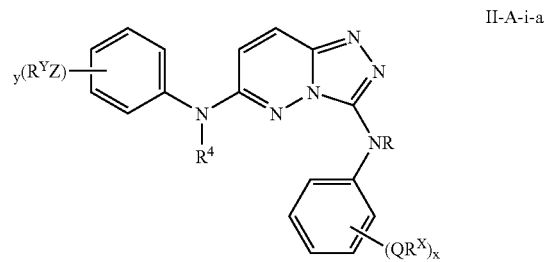

II-A-i-a

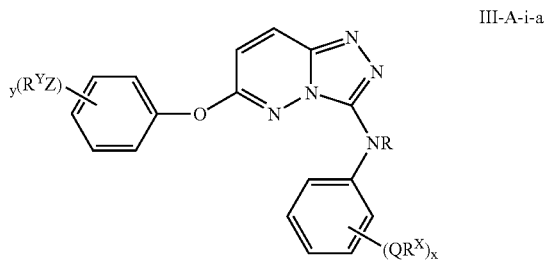

III-A-i-a

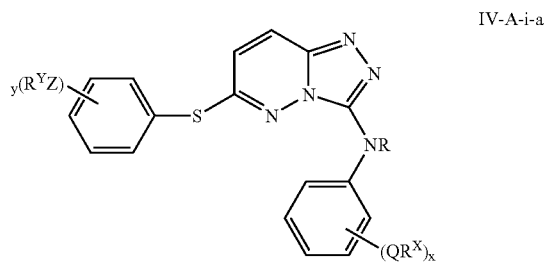

IV-A-i-a

-continued
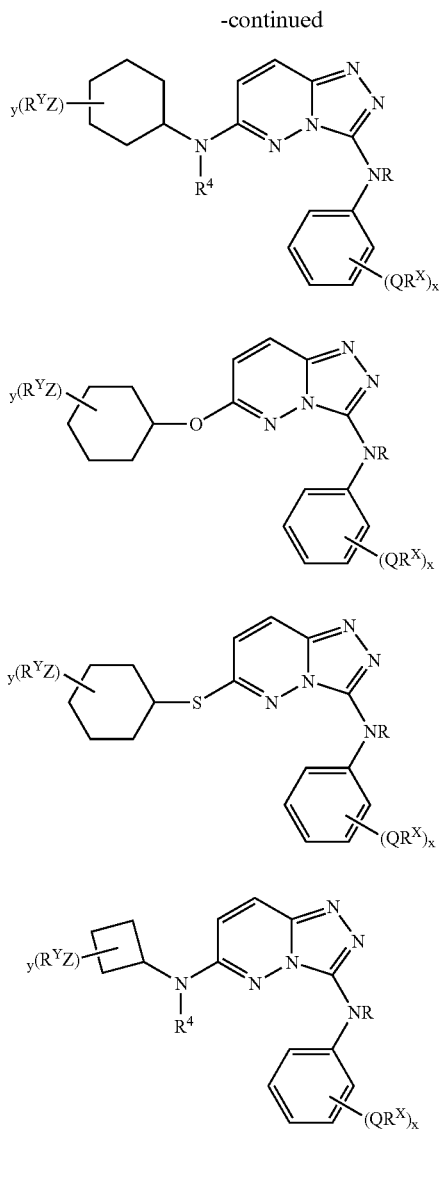
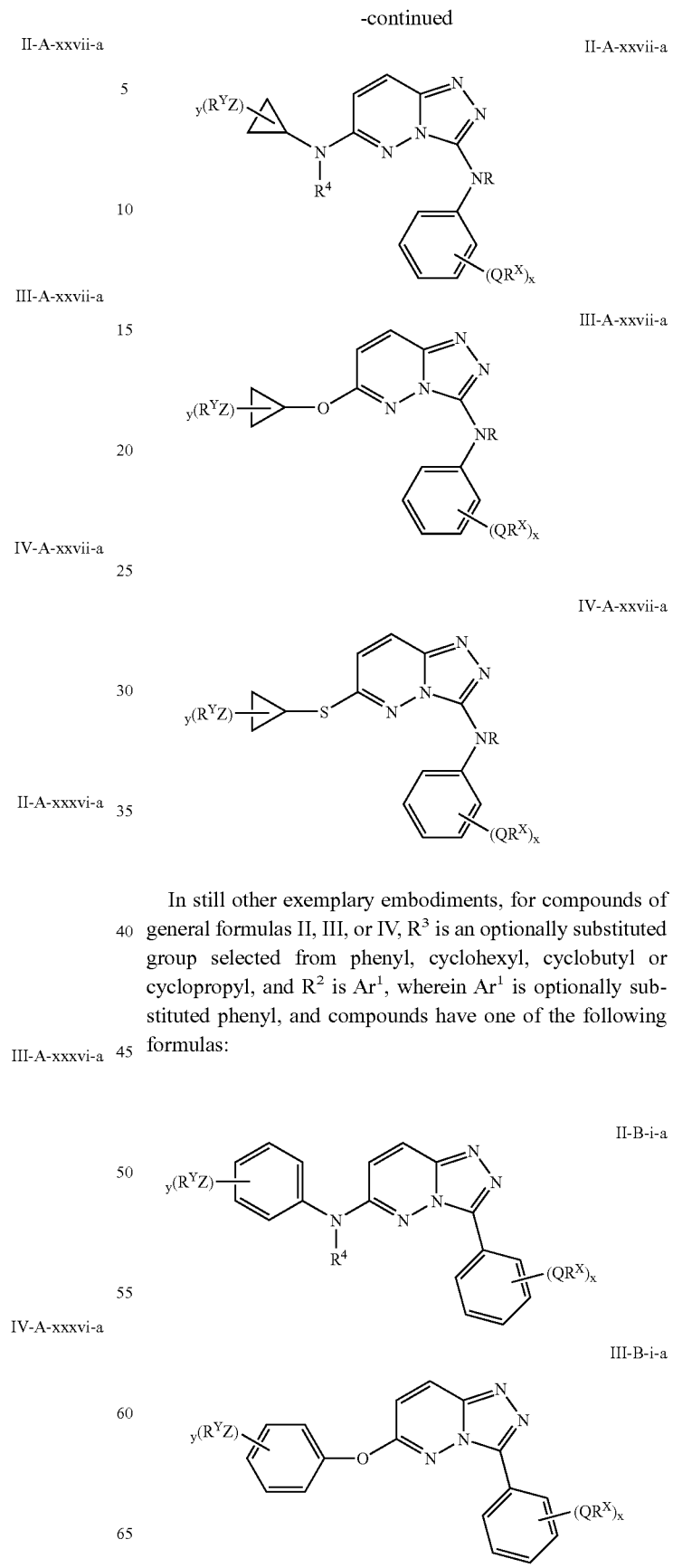
In still other exemplary embodiments, for compounds of general formulas II, III, or IV, $R^3$ is an optionally substituted group selected from phenyl, cyclohexyl, cyclobutyl or cyclopropyl, and $R^2$ is $Ar^1$, wherein $Ar^1$ is optionally substituted phenyl, and compounds have one of the following formulas:

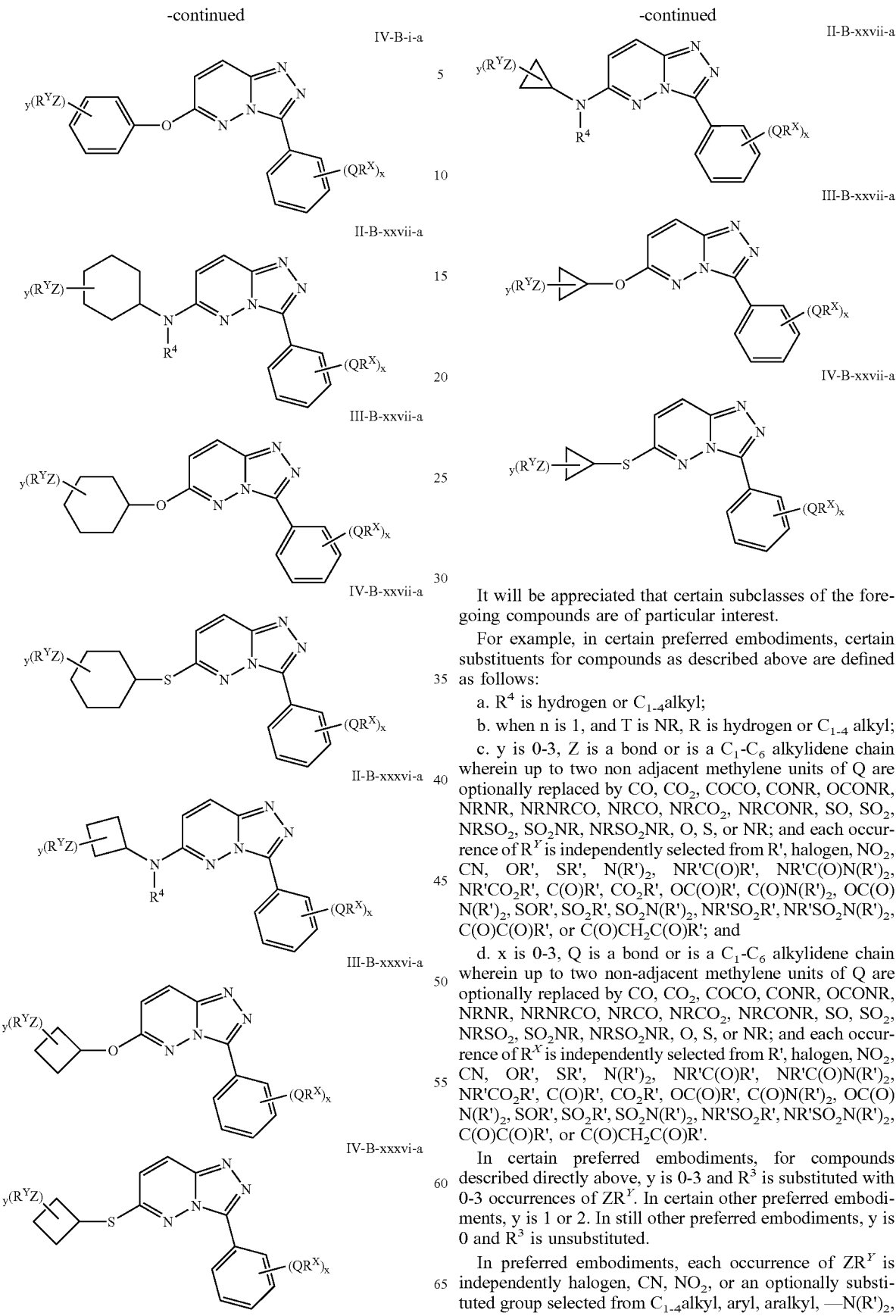

It will be appreciated that certain subclasses of the foregoing compounds are of particular interest.

For example, in certain preferred embodiments, certain substituents for compounds as described above are defined as follows:

a. $R^4$ is hydrogen or $C_{1-4}$alkyl;

b. when n is 1, and T is NR, R is hydrogen or $C_{1-4}$ alkyl;

c. y is 0-3, Z is a bond or is a $C_1$-$C_6$ alkylidene chain wherein up to two non adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of $R^Y$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'; and d. x is 0-3, Q is a bond or is a $C_1$-$C_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of $R^X$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'.

In certain preferred embodiments, for compounds described directly above, y is 0-3 and $R^3$ is substituted with 0-3 occurrences of $ZR^Y$. In certain other preferred embodiments, y is 1 or 2. In still other preferred embodiments, y is 0 and $R^3$ is unsubstituted.

In preferred embodiments, each occurrence of $ZR^Y$ is independently halogen, CN, NO$_2$, or an optionally substituted group selected from $C_{1-4}$alkyl, aryl, aralkyl, —N(R')$_2$, CH$_2$N(R')$_2$, —OR', CH$_2$OR', —SR', CH$_2$SR', COOR', or —S(O)₂N(R')₂. In more preferred embodiments, each occurrence of $ZR^Y$ is independently Cl, Br, F, CN, CF₃, COOH, —N(CH₃)₂, —OH, CH₂OH, or an optionally substituted group selected from $C_{1-4}$alkoxy, $C_{1-4}$alkyl, phenyl, phenyloxy, benzyl, or benzyloxy. Most preferred $ZR^Y$ groups include those shown below in Table 1.

In certain preferred embodiments for compounds described directly above, x is 0-3 and R² is substituted with 0-3 occurrences of $QR^X$. In certain other preferred embodiments, x is 1 or 2. In still other preferred embodiments, x is 0 and R² is unsubstituted.

In preferred embodiments, each occurrence of $QR^X$ is independently halogen, CN, NO₂, or an optionally substituted group selected from $C_{1-4}$alkyl, aryl, aralkyl, —N(R')₂, CH₂N(R')₂, —OR', CH₂OR', —SR', CH₂SR', COOR', or —S(O)₂N(R')₂. In more preferred embodiments, each occurrence of $QR^X$ is independently Cl, Br, F, CN, CF₃, COOH, —N(CH₃)₂, —OH, CH₂OH, or an optionally substituted group selected from $C_{1-4}$alkoxy, $C_{1-4}$alkyl, phenyl, phenyloxy, benzyl, or benzyloxy. Most preferred $QR^X$ groups include those shown below in Table 1.

Representative examples of compounds of formula I are set forth below in Table 1.

TABLE 1

Examples of Compounds of Formula I:

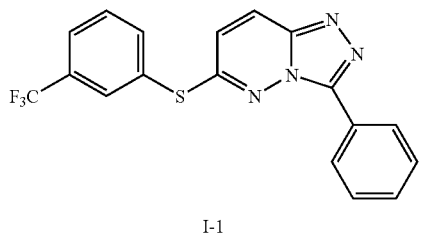

I-1

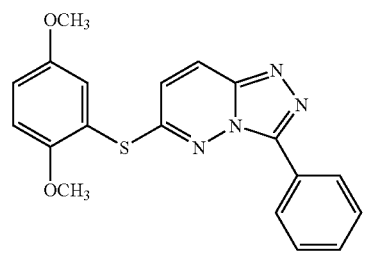

I-2

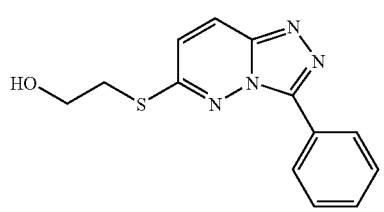

I-3

TABLE 1-continued

Examples of Compounds of Formula I:

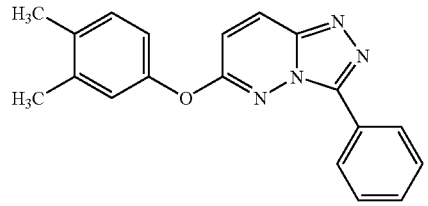

I-4

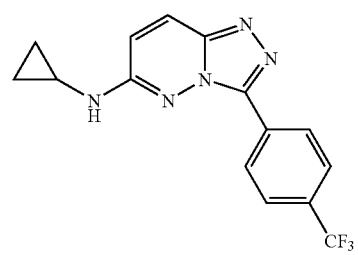

I-5

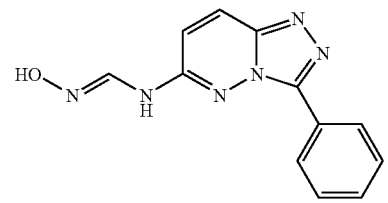

I-6

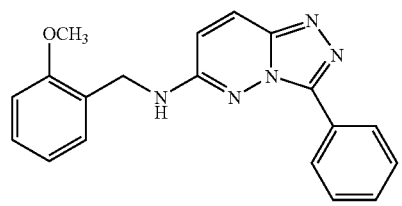

I-7

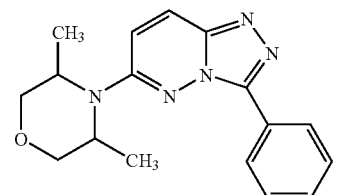

I-8

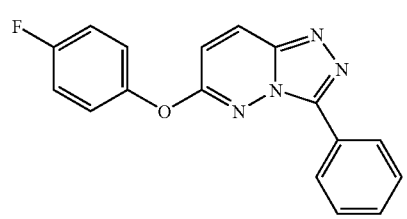

I-9

TABLE 1-continued
Examples of Compounds of Formula I:
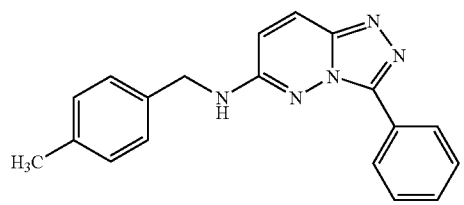
I-10
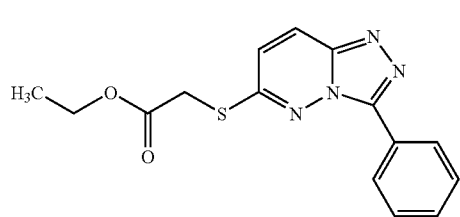
I-11
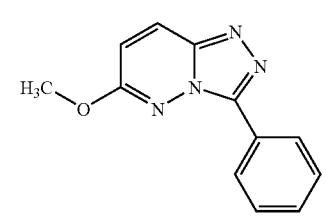
I-12
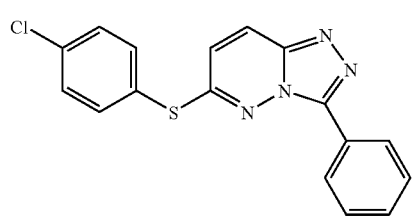
I-13
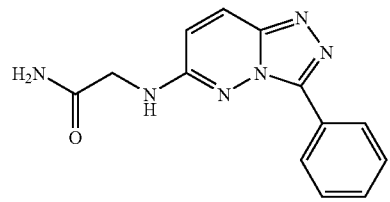
I-14
I-15
TABLE 1-continued
Examples of Compounds of Formula I:
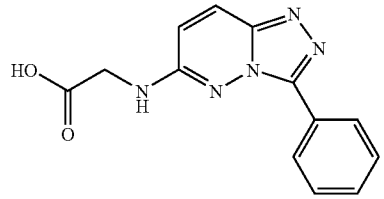
I-16
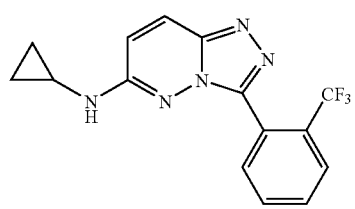
I-17
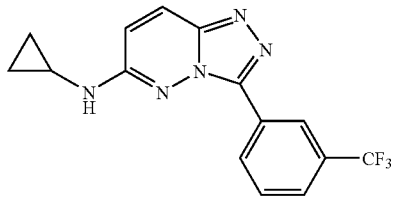
I-18
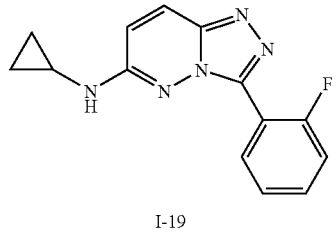
I-19
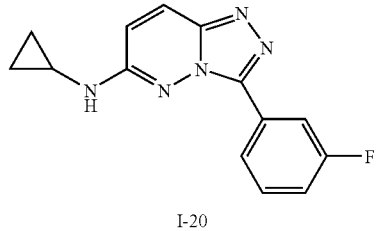
I-20
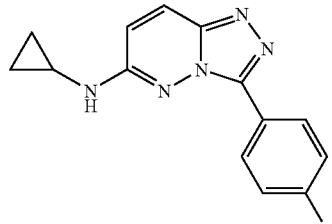
I-21

TABLE 1-continued
Examples of Compounds of Formula I:
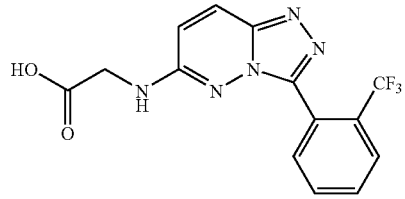
I-22
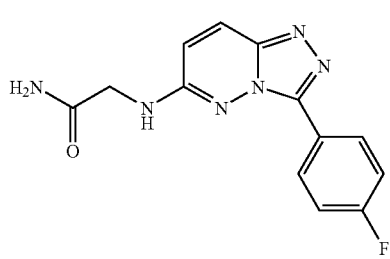
I-23
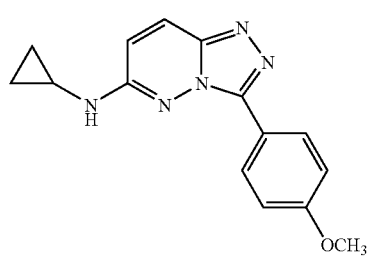
I-24
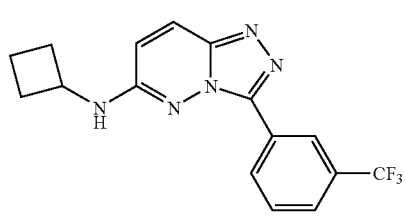
I-25
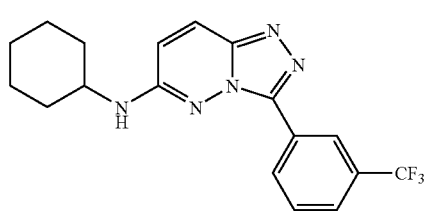
I-26
TABLE 1-continued
Examples of Compounds of Formula I:
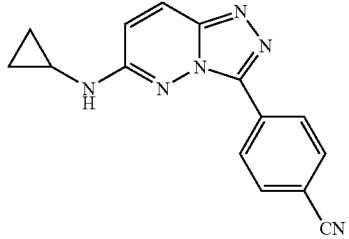
I-27
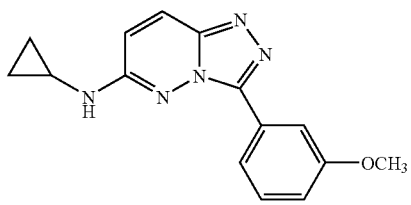
I-28
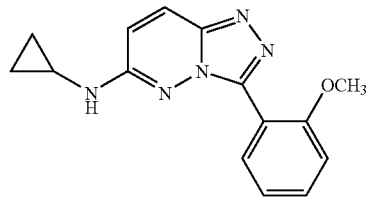
I-29
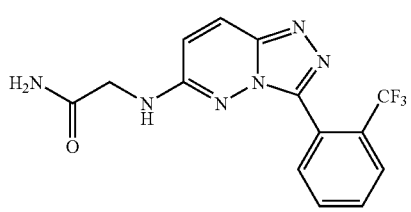
I-30
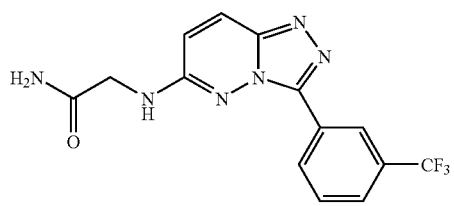
I-31
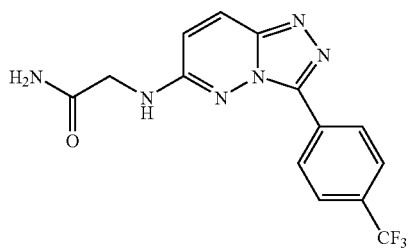
I-32

TABLE 1-continued
Examples of Compounds of Formula I:
I-33
I-34
I-35
I-36
I-37
I-38
TABLE 1-continued
Examples of Compounds of Formula I:
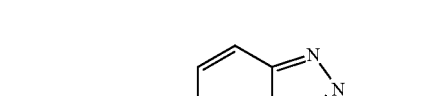
I-39
I-40
I-41
I-43
I-44

TABLE 1-continued
Examples of Compounds of Formula I:
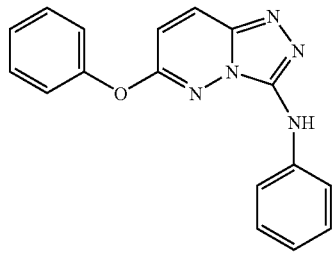
I-45
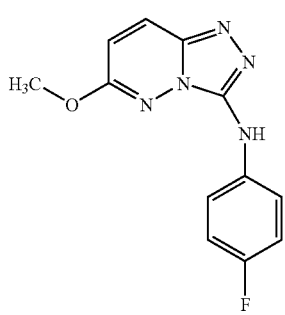
I-46
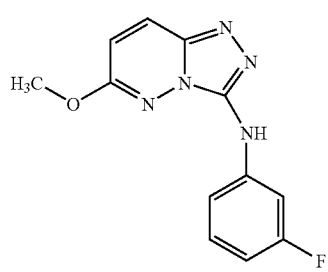
I-47
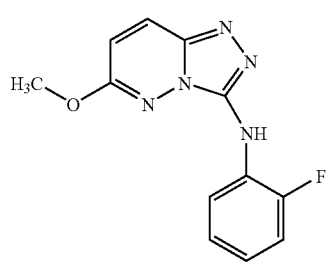
I-48
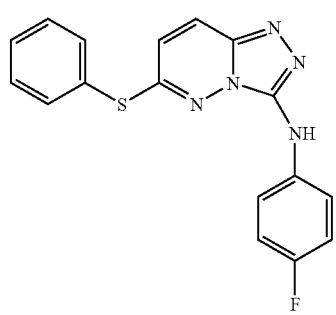
I-49
TABLE 1-continued
Examples of Compounds of Formula I:
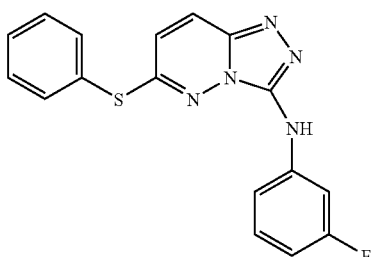
I-50
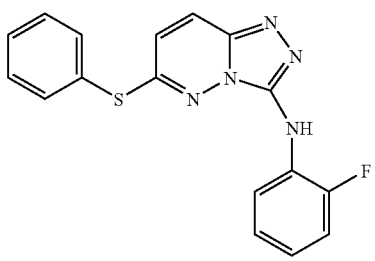
I-51
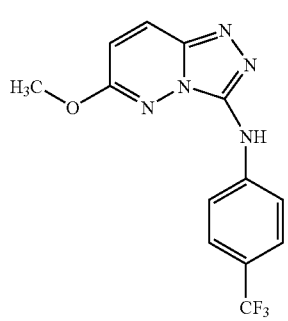
I-52
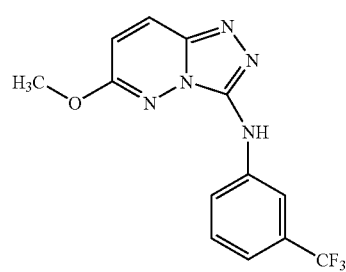
I-53
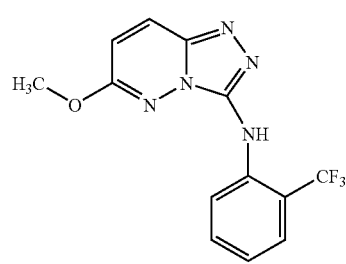
I-54

TABLE 1-continued
Examples of Compounds of Formula I:
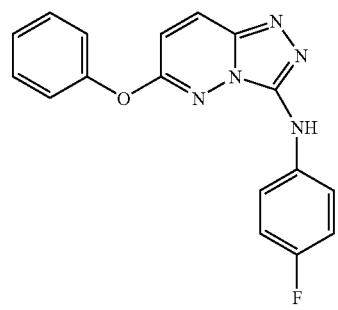
I-55
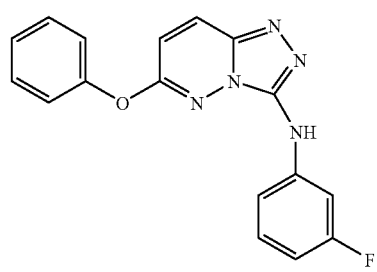
I-56
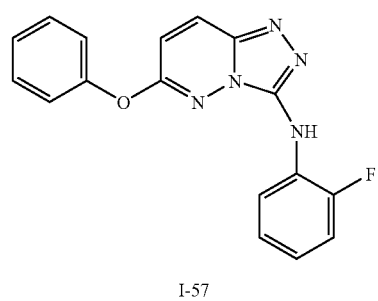
I-57
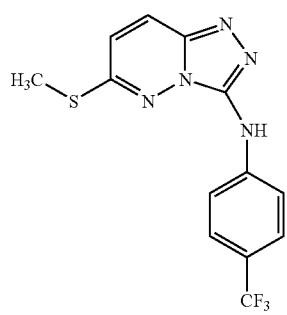
I-58
TABLE 1-continued
Examples of Compounds of Formula I:
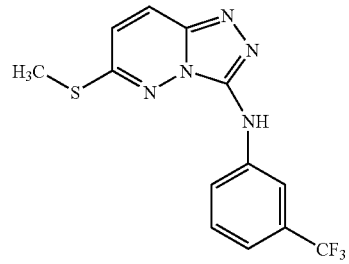
I-59
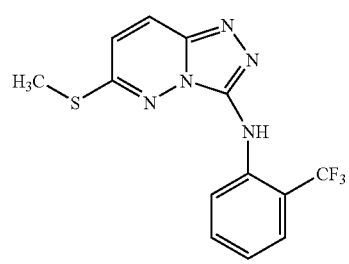
I-60
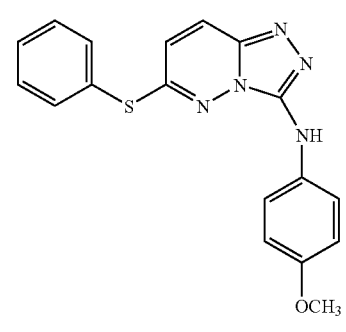
I-61
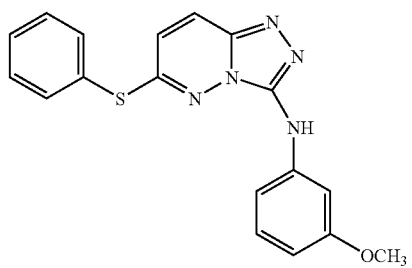
I-62
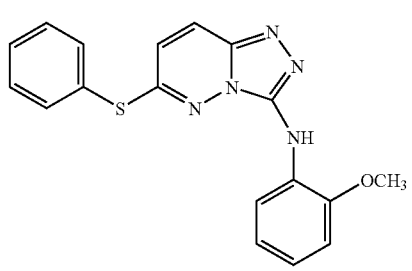
I-63

TABLE 1-continued
Examples of Compounds of Formula I:
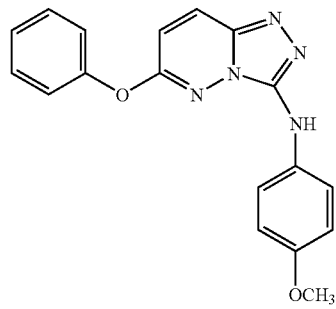
I-64
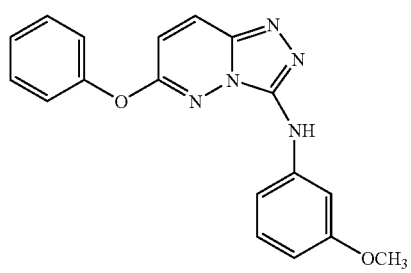
I-65
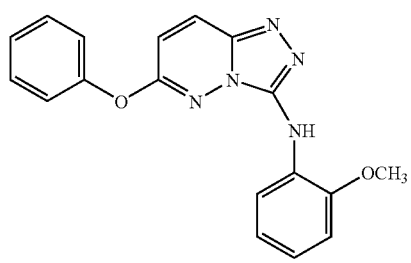
I-66
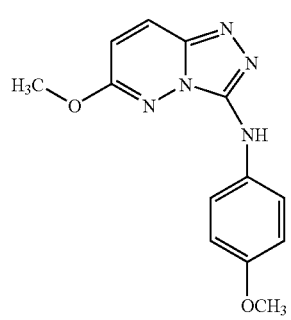
I-67
TABLE 1-continued
Examples of Compounds of Formula I:
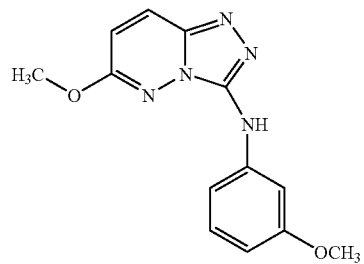
I-68
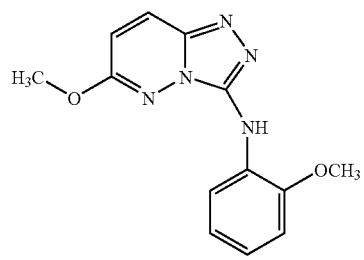
I-69
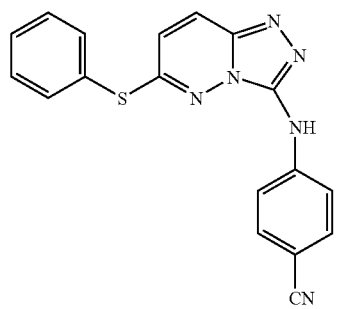
I-70
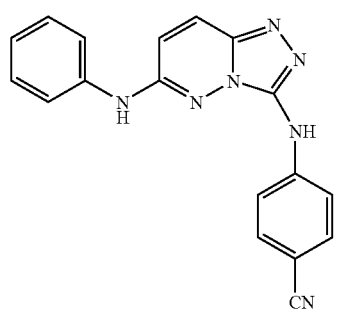
I-71

TABLE 1-continued
Examples of Compounds of Formula I:
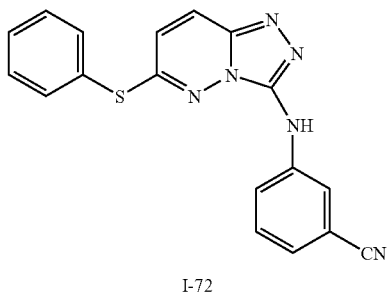
I-72
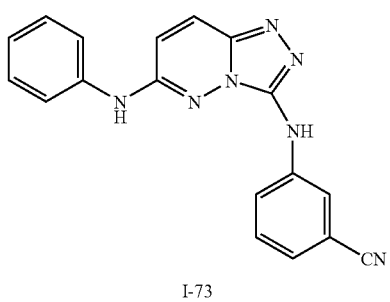
I-73
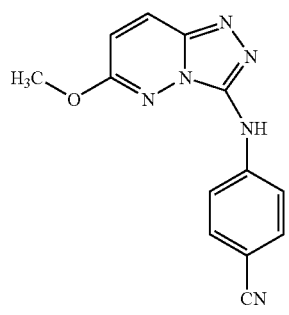
I-74
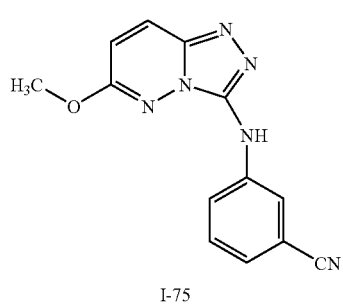
I-75
TABLE 1-continued
Examples of Compounds of Formula I:
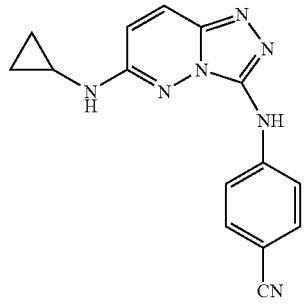
I-76
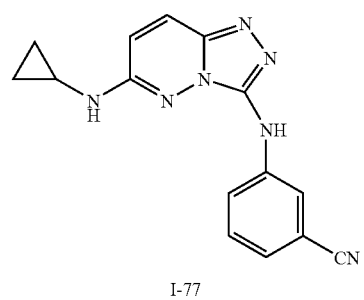
I-77
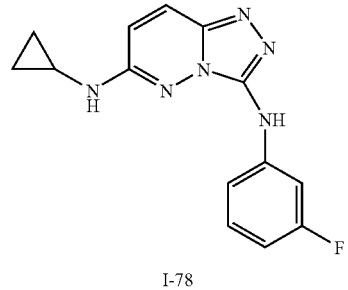
I-78
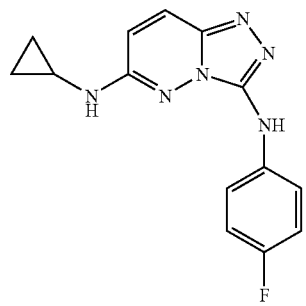
I-79
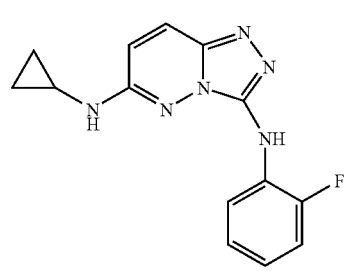
I-80

TABLE 1-continued
Examples of Compounds of Formula I:
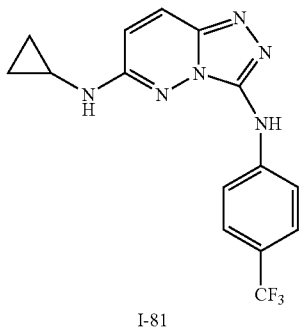
I-81
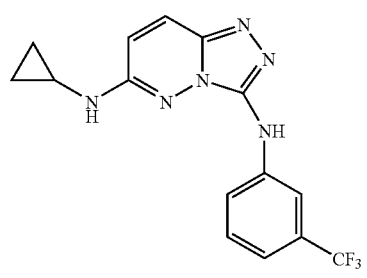
I-82
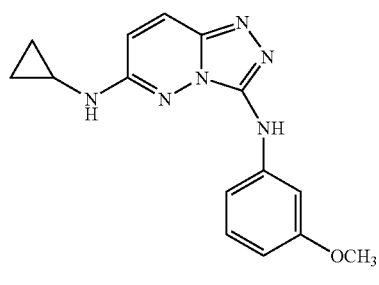
I-83
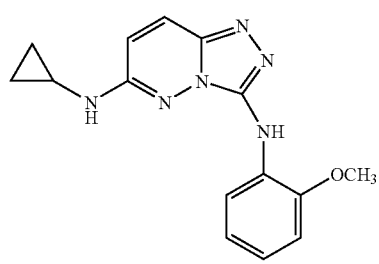
I-84
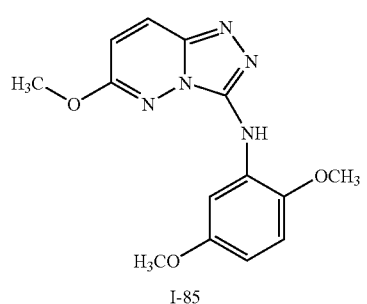
I-85
TABLE 1-continued
Examples of Compounds of Formula I:
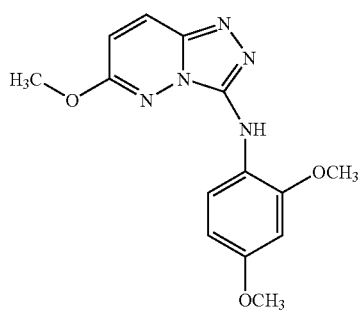
I-86
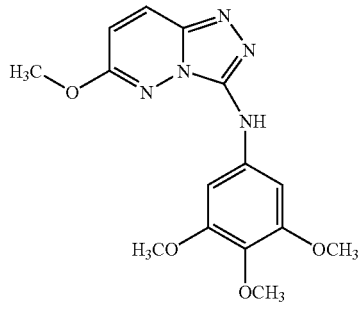
I-87
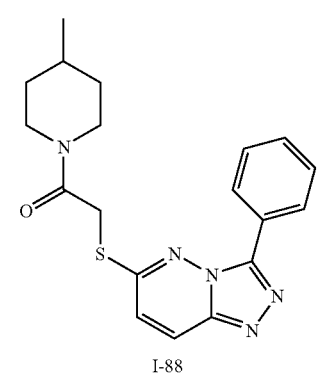
I-88
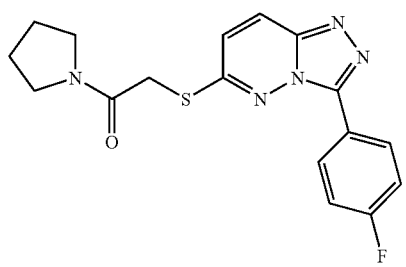
I-89

TABLE 1-continued
Examples of Compounds of Formula I:
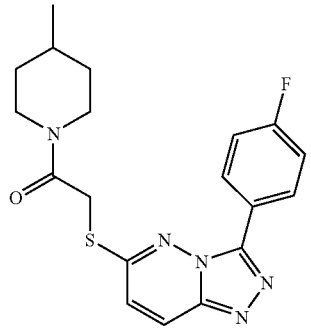
I-90
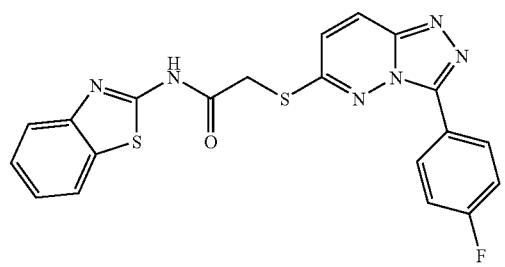
I-91
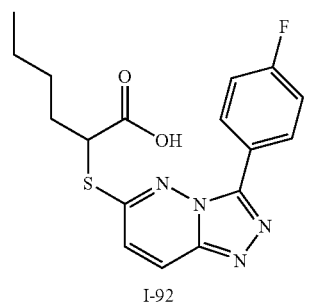
I-92
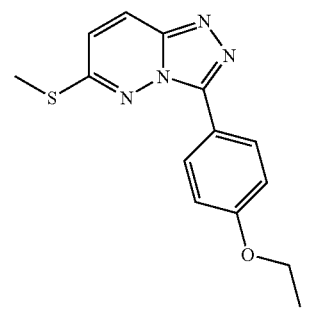
I-93
TABLE 1-continued
Examples of Compounds of Formula I:
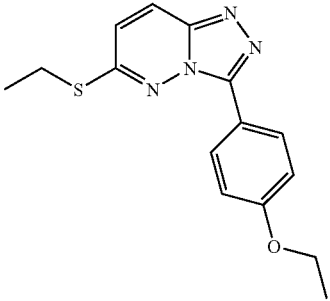
I-94
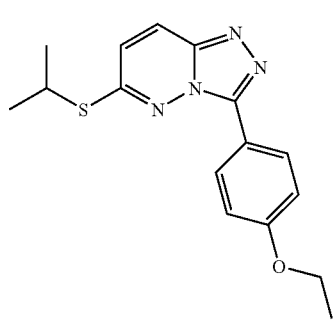
I-95
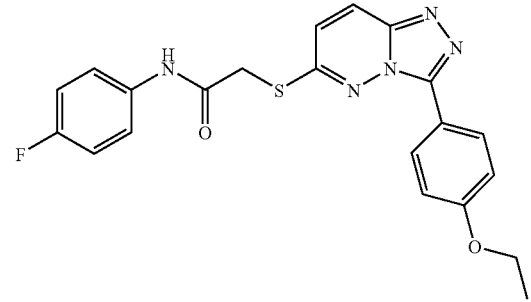
I-96
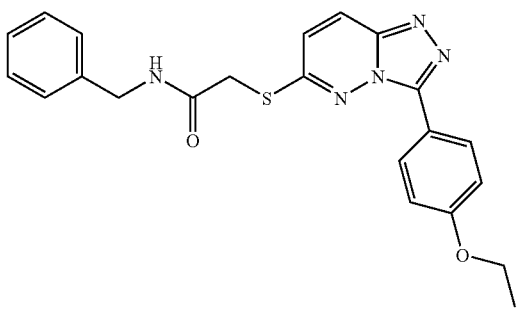
I-97

53

TABLE 1-continued

Examples of Compounds of Formula I:

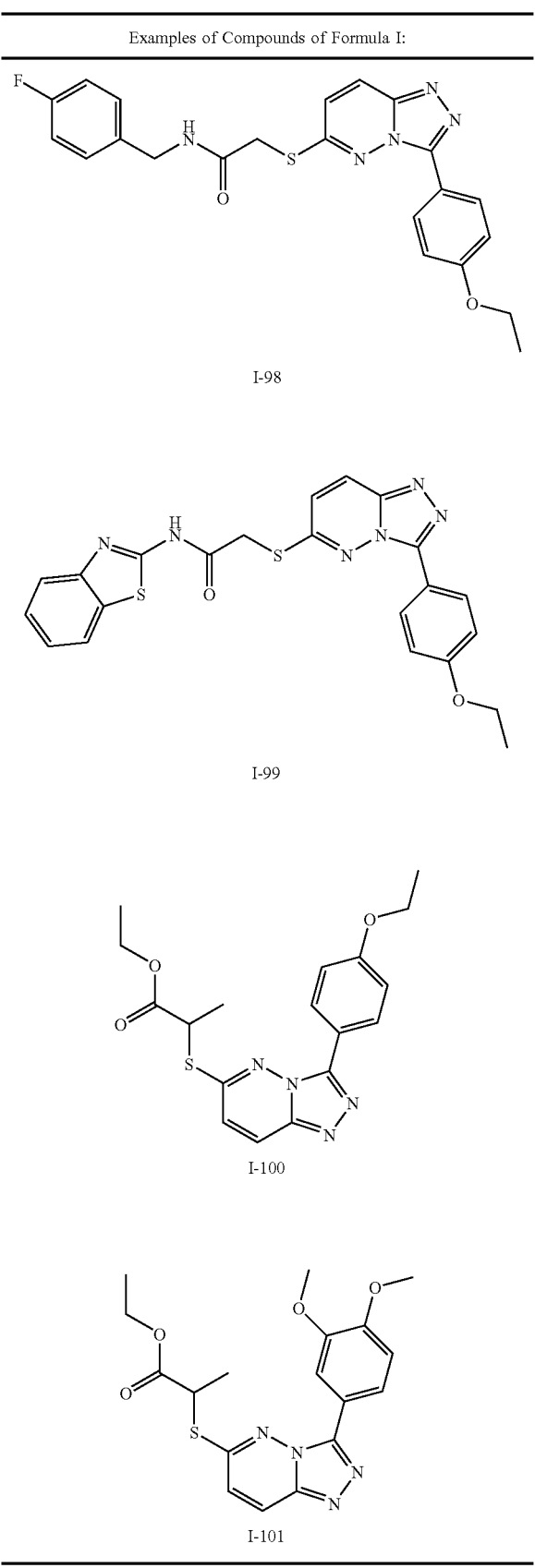

I-98

I-99

I-100

I-101

54

4. General Synthetic Methodology

The compounds of this invention may be prepared in general by methods known to those skilled in the art for analogous compounds, as illustrated by the general scheme below, and the preparative examples that follow.

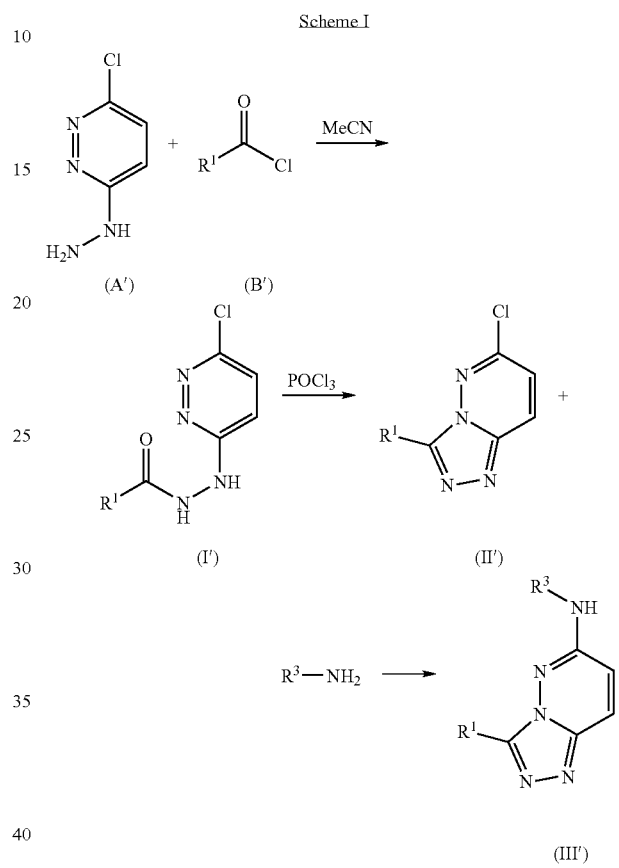

Scheme 1 above shows a general method for preparing compounds of formula III'. For example, compounds of the invention can be prepared by reaction of starting material (A) with POCl₃ yields chloride (II'). Reaction of (II') with an appropriate amine yields desired compounds of general formula (III').

Scheme 2 below depicts the synthesis of certain exemplary compounds where $R^2$ is phenyl, which compounds are also prepared according to the general procedures described above.

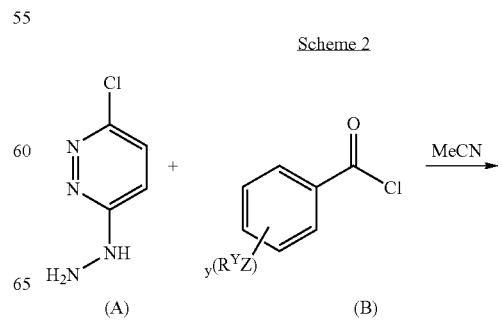

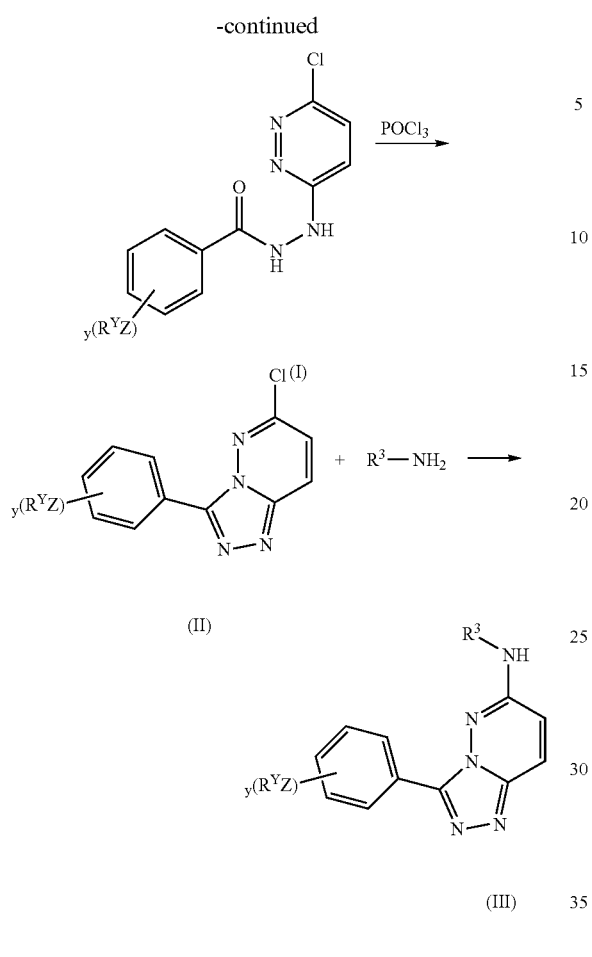
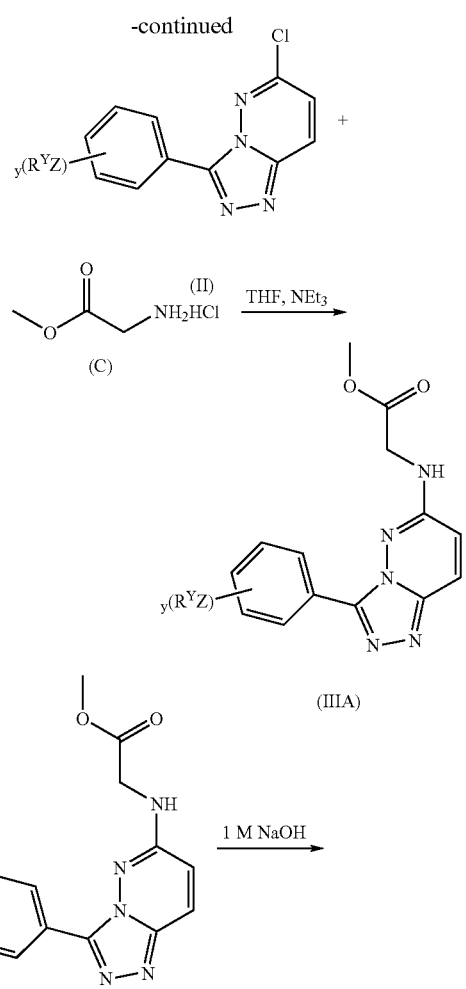
Scheme 3 below depicts the synthesis of certain exemplary compounds where $R^2$ is phenyl, and $R^1$ is $NHR^3$, wherein $R^3$ is $(CH_2)(C=O)OH$, which compounds are also prepared according to the general procedures described above.
Scheme 3
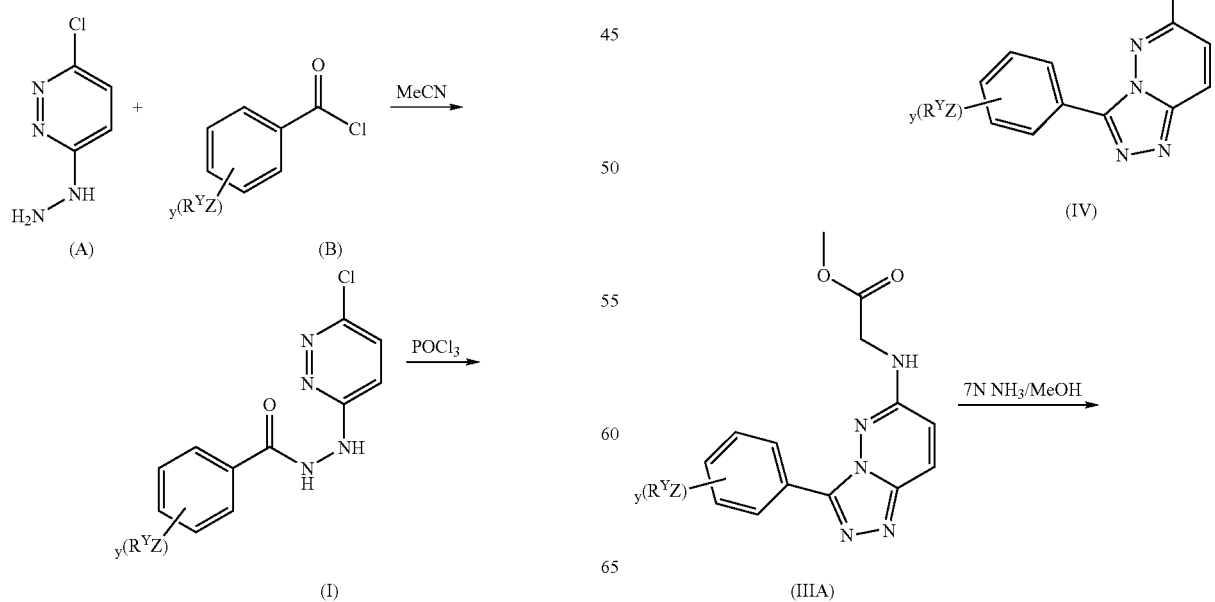

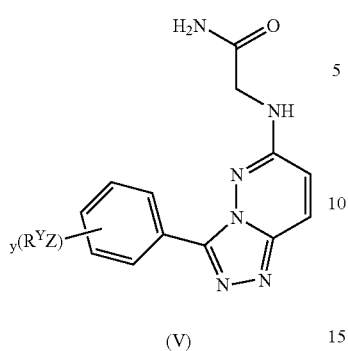

Scheme 4 below depicts the synthesis of certain exemplary compounds where R² is (T)ₙAr¹, and n is 1, T is NH, and Ar¹ is optionally substituted phenyl, which compounds are also prepared according to the general procedures described above.

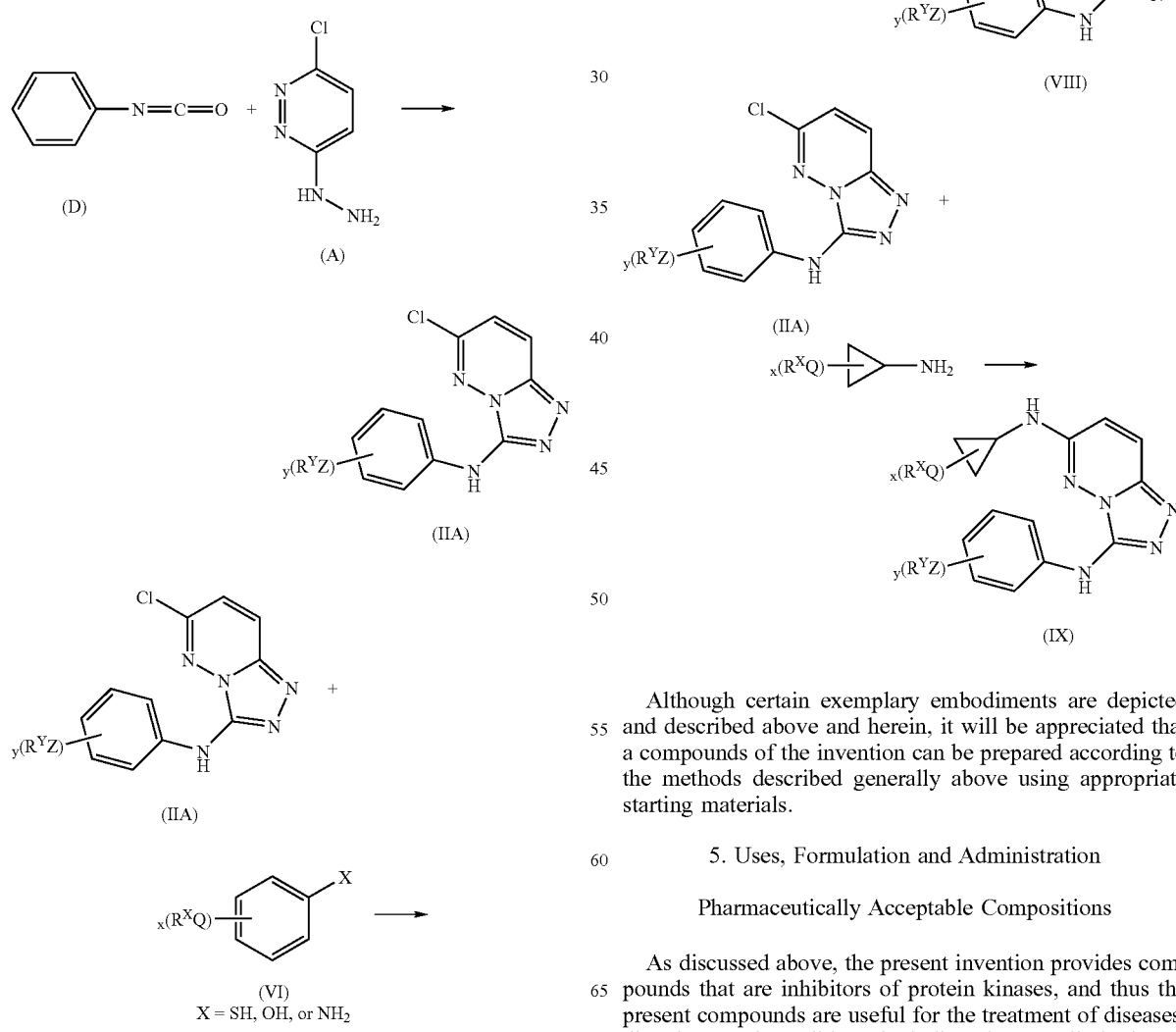

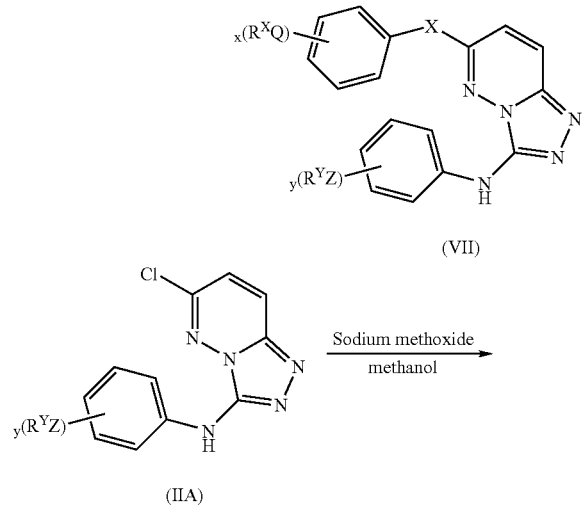

Although certain exemplary embodiments are depicted and described above and herein, it will be appreciated that a compounds of the invention can be prepared according to the methods described generally above using appropriate starting materials.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to a proliferative disorder, a cardiac disorder, a neurodegenerative disorder, psychotic disorders, an autoimmune disorder, a condition associated with organ transplant, an inflammatory disorder, an immunologically mediated disorder, a viral disease, or a bone disorder. In preferred embodiments, the compounds are useful for the treatment of allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia (e.g., stroke), baldness, cancer, hepatomegaly, cardiovascular disease including cardiomegaly, cystic fibrosis, viral disease, autoimmune diseases, atherosclerosis, restenosis, psoriasis, inflammation, hypertension, angina pectoris, cerebrovascular contraction, peripheral circulation disorder, premature birth, arteriosclerosis, vasospasm (cerebral vasospasm, coronary vasospasm), retinopathy, erectile dysfunction (ED), AIDS, osteoporosis, Crohn's Disease and colitis, neurite outgrowth, and Raynaud's Disease. In preferred embodiments, the disease, condition, or disorder is atherosclerosis, hypertension, erectile dysfunction (ED), reperfusion/ischemia (e.g., stroke), or vasospasm (cerebral vasospasm and coronary vasospasm).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a PIM-1, CDK-2, SRC, or GSK-3.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of PIM-1, CDK-2, SRC, or GSK-3, and thus, without wishing to be bound by any particular theory, the compounds and compositions are particularly useful for treating or lessening the severity of a disease, condition, or disorder where activation of one or more of PIM-1, CDK-2, SRC, or GSK-3 is implicated in the disease, condition, or disorder. When activation of PIM-1, CDK-2, SRC, or GSK-3 is implicated in a particular disease, condition, or disorder, the disease, condition, or disorder may also be referred to as "PIM-1, CDK-2, SRC, or GSK-3-mediated disease" or disease symptom. Accordingly, in another aspect, the present invention provides a method for treating or lessening the severity of a disease, condition, or disorder where activation or one or more of PIM-1, CDK-2, SRC, or GSK-3 is implicated in the disease state.

The activity of a compound utilized in this invention as an inhibitor of PIM-1, CDK-2, SRC, or GSK-3, may be assayed in vitro, in vivo or in a cell line. In vitro assays include assays that determine inhibition of either the phosphorylation activity or ATPase activity of activated PIM-1, CDK-2, SRC, or GSK-3. Alternate in vitro assays quantitate the ability of the inhibitor to bind to PIM-1, CDK-2, SRC, or GSK-3. Inhibitor binding may be measured by radiolabelling the inhibitor prior to binding, isolating the inhibitor/PIM-1, CDK-2, SRC, or GSK-3 complex and determining the amount of radiolabel bound. Alternatively, inhibitor binding may be determined by running a competition experiment where new inhibitors are incubated with PIM-1, CDK-2, SRC, or GSK-3 bound to known radioligands.

The term "measurably inhibit", as used herein means a measurable change in PIM-1, CDK-2, SRC, or GSK-3 activity between a sample comprising said composition and a PIM-1, CDK-2, SRC, or GSK-3 kinase and an equivalent sample comprising PIM-1, CDK-2, SRC, or GSK-3 kinase in the absence of said composition.

The term "PIM-mediated disease", as used herein means any disease or other deleterious condition in which a PIM family kinase is known to play a role. Such conditions include, without limitation, cancer, particularly lymphomas, inflammatory disease, including asthma, allergy, and Crohn disease, and immunosuppression, including transplantation rejection, and autoimmune disease.

The term "CDK-2-mediated disease", as used herein means any disease or other deleterious condition in which CDK-2 is known to play a role. Accordingly, these compounds are useful for treating diseases or conditions that are known to be affected by the activity of CDK-2 kinase. Such diseases or conditions include cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis, viral infections, neurodegenerative disorders, disorders associated with thymocyte apoptosis, or proliferative disorders resulting from the deregulation of the cell cycle, especially of the progression from $G_1$ to S phase.

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases (e.g., Alzheimer's disease, Huntington's disease, Parkinson's disease and basal ganglia movement disorders, chorea, dystonia, Wilson Disease, Pick Disease, frontal lobe degeneration, progressive supranuclear palsy (PSP), Creutzfeldt-Jakob Disease, taupathology and corticobasal degeneration (CBD)), psychotic disorders (e.g., schizophrenia, AIDS-associated dementia, depression, bipolar disorder, and anxiety disorders), cardiovascular diseases, allergy, asthma, diabetes, amyotrophic lateral sclerosis (AML, Lou Gehrig's disease), multiple sclerosis (MS), cardiomyocyte hypertrophy, reperfusion/ischemia, stroke, and baldness.

The term "Src-mediated disease" as used herein means any disease or other deleterious condition in which Src kinase plays a role. Such diseases or conditions include, without limitation, cancers such as colon, breast, hepatic and pancreatic cancer, autoimmune diseases such as transplant rejection, allergies, rheumatoid arthritis, leukemia, bone remodeling diseases such as osteoporosis and viral diseases such as hepatitis B infection.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting PIM-1, CDK-2, SRC, or GSK-3 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of PIM-1, CDK-2, SRC, or GSK-3 kinase activity in a biological sample is useful for a variety of purposes that are known to one of skill in the art. Examples of such purposes include, but are not limited to, blood transfusion, organ-transplantation, biological specimen storage, and biological assays.

In order that the invention described herein may be more fully understood, the following examples are set forth. It should be understood that these examples are for illustrative purposes only and are not to be construed as limiting this invention in any manner.

EXAMPLES

Example 1

Synthesis of Exemplary Compounds of the Invention

Certain exemplary compounds as shown generally in Scheme 2 were prepared according to the general procedure as follows:

The starting material (A) was dissolved to 0.5M solution in MeCN and stirred at room temperature for 2 hours. HPLC and mass spectrometry confirmed the formation of (I). To the same solution, phosphorus oxychloride was added in an equal amount by volume to the acetonitrile already present. The reaction was allowed to proceed at 80° C. overnight. Upon complete reaction, the mixture was then poured over ice and stirred for 1 hour. Followed by aqueous workup and extraction with ethyl acetate. The organic layer was dried with magnesium sulfate, filtrated and concentrated to dryness. The crude material was purified by silica gel column chromatography.

40-400 mg of (II) were dissolved in 0.5 to 1.0 mL of cycloalkylamine and heated to 70° C. for 4 hours. The reaction was concentrated to dryness and purified by reversed-phase preparative HPLC.

Certain exemplary compounds as shown generally in Scheme 3 were prepared according to the following general procedures:

The starting material (A) was dissolved to 0.5M solution in MeCN and stirred at room temperature for 2 hours. HPLC and mass spectrometry confirmed the formation of (I). To the same solution, phosphorus oxychloride was added in an equal amount by volume to the acetonitrile already present. The reaction was allowed to proceed at 80° C. overnight. Upon complete reaction, the mixture was then poured over ice and stirred for 1 hour. Followed by aqueous workup and extraction with ethyl acetate. The organic layer was dried with magnesium sulfate, filtrated and concentrated to dryness. The crude material was purified by silica gel column chromatography.

(II) was dissolved in a 1M solution of THF followed by the addition of 5 equivalent of the glycine methyl ester hydrochloride and 5 equivalents of triethylamine. The reaction tube was sealed and heated to 130° C. for 48 hours. The reaction was concentrated to dryness, extracted with ethyl acetate and water, dried over $MgSO_4$, and the solution concentrated to dryness. The product was purified by reversed-phase preparative HPLC.

(IIIA) was dissolved in 1M aqueous NaOH and heated to reflux for 2 hours. The crude reaction was concentrated to dryness. The product (IV) was purified by reversed-phase preparative HPLC.

(IIIA) was dissolved in 7N $NH_3$ in MeOH and heated to reflux for 4 hours. The crude reaction was concentrated to dryness. The product (V) was purified by reversed-phase preparative HPLC.

Certain exemplary compounds as shown generally in Scheme 4 were prepared according to the following general procedures:

Starting materials A and I are commercially available, and the preparation of Intermediate IIA is described in: "A Mild Approach to 1,3,4-Oxadiazoles and Fused 1,2,4-Triazoles. Diazenes as Intermediates?" Janez Kosmrlj, Marijan Kocevar, Slovenko Polanc, *Synlett*, 7, 652 (1996).

General Experimentals (VI): The starting material (IIA) was dissolved in a 1 M solution of N-methylpyrrolidone followed by the addition of (VI) and heated to 100° C. overnight. The reaction was checked by HPLC and MS+ to be complete and was then concentrated to dryness. The products were purified by preparative reversed-phase HPLC.

(VIII): The starting material (IIA) was dissolved in methanol containing 5 equivalents of sodium methoxide.

The reaction was heated to reflux for 4 hours. The crude material was purified by preparative reversed-phase HPLC.

(IX): The starting material (IIA) was dissolved in 500 μl of cyclopropylamine. The tube was sealed and heated to 70° C. for 4 hours. Upon completion the reactions were then concentrated to dryness, then purified by preparative reversed-phase HPLC.

Table 2 below depicts exemplary data for certain compounds of the invention:

| Compound Number | MSpos | NMR |
|---|---|---|
| I-5 | 320.2 | DMSO-d6: 8.80(d, 2H), 8.07(d, 1H), 7.98(d, 2H), 7.90(s, 1H), 6.85(d, 1H), 2.75(m, 1H), 0.90(m, 2H), 0.58(m, 2H) |
| I-14 | 269.2 | DMSO-d6: 8.52(m, 2H), 8.04(d, 1H), 7.90(m, 2H), 7.65(s, 1H), 7.35(m, 2H), 7.20(s, 1H), 7.00 (d, 1H), 3.89(d, 2H) |
| I-15 | 252.2 | MeOH-d4: 8.55(m, 2H), 7.98(d, 1H), 7.60(m, 3H), 7.07(d, 1H), 2.78(m, 1H), 0.92(m, 2H), 0.65(m, 2H) |
| I-16 | 270.1 | MeOH-d4: 8.45(d, 2H), 7.85(d, 1H), 7.57(t, 2H), 7.50(t, 1H), 7.00(d, 1H), 3.95(s, 2H) |
| I-17 | 320.1 | MeOH-d4: 7.97(m, 1H), 7.93(d, 1H), 7.84(m, 2H), 7.77(m, 1H), 7.00(d, 1H), 2.50(m, 1H), 0.65(m, 2H), 0.46(m, 2H) |
| I-18 | 320.2 | DMSO-d6: 9.15(s, 1H), 8.75(d, 1H), 8.07(d, 1H), 7.92(s, 1H), 7.88(d, 1H), 7.81(t, 1H), 6.84 (d, 1H), 2.70(m, 1H), 0.84(m, 2H), 0.59(m, 2H) |
| I-19 | 270.1 | DMSO-d6: 8.05(m, 2H), 7.75(s, 1H), 7.62(m, 1H), 7.45(m, 2H), 6.86(d, 1H), 2.59(m, 1H), 0.72(m, 2H), 0.50(m, 2H) |
| I-20 | 270.1 | DMSO-d6: 8.48(d, 1H), 8.40(d, 1H), 8.05(d, 1H), 7.87(s, 1H), 7.62(m, 1H), 7.36(m, 1H), 6.82(d, 1H), 2.70(m, 1H), 0.85(m, 2H), 0.60(m, 2H) |
| I-21 | 270.1 | DMSO-d6: 8.62(m, 2H), 8.00(d, 1H), 7.81(s, 1H), 7.42(m, 2H), 6.80(d, 1H), 2.69(m, 1H), .085(m, 2H), 0.57(m, 2H) |
| I-22 | 338.2 | MeOH-d4: 7.86(m, 1H), 7.82(m, 1H), 7.81(m, 1H), 7.80-7.79(m, 1H), 7.67(m, 1H), 7.01(d, 1H), 3.70(m, 2H) |
| I-23 | 287.2 | DMSO-d6: 8.52(m, 2H), 8.04(d, 1H), 7.90(m, 1H), 7.65(s, 1H), 7.35(m, 2H), 7.20(s, 1H), 7.00 (d, 1H), 3.89(d, 2H) |
| I-24 | 282.5 | MeOH-d4: 8.50(d, 2H), 7.95(d, 1H), 7.15(d, 2H), 7.05(d, 1H), 3.90(s, 3H), 2.78(m, 1H), 0.91(m, 2H), 0.64(m, 2H) |
| I-25 | 334.2 | MeOH-d4: 9.04(s, 1H), 8.65(d, 1H), 7.92(d, 1H), 7.85(d, 1H), 7.79(t, 1H), 4.34(m, 1H), 2.52 (m, 2H), 2.05(m, 2H), 1.90(m, 2H) |
| I-26 | 362.4 | DMSO-d6: 8.97(s, 1H), 8.64(d, 1H), 8.03(d, 1H), 7.89(d, 1H), 7.82(t, 1H), 7.52(d, 1H), 6.90 (d, 1H), 3.66(m, 1H), 2.07(m, 2H), 1.76(m, 2H), 1.65(m, 1H), 1.30(m, 5H) |
| I-27 | 277.2 | DMSO-d6: 8.79(d, 2H), 8.06(d, 3H), 7.91(s, 1H), 6.85(d, 1H), 2.70(m, 1H), 0.88(m, 2H), 0.55(m, 2H) |
| I-28 | 282.3 | DMSO-d6: 8.21(s, 1H), 8.15(d, 1H), 8.04(d, 1H), 7.85(m, 1H), 7.50(t, 1H), 7.10(d, 1H), 6.85 (d, 1H), 3.85(s, 3H), 2.71(m, 1H), 0.81(m, 2H), 0.56(m, 2H) |
| I-29 | 282.2 | MeOH-d4: 8.32(d, 1H), 7.98(d, 1H), 7.67(t, 1H), 7.32(d, 1H), 7.25(t, 1H), 7.08(d, 1H), 2.70 (m, 1H), 0.82(m, 2H), 0.60(m, 2H) |
| I-30 | 337.2 | DMSO-d6: 8.05(d, 1H), 7.96(d, 1H), 7.81(m, 3H), 7.61(m, 1H), 7.43(m, 1H), 7.10(d, 2H), 3.68(m, 2H) |
| I-31 | 337.2 | DMSO-d6: 8.83(d, 1H), 8.71(d, 1H), 8.10(d, 1H), 7.90(m, 2H), 7.81(t, 1H), 7.58(s, 1H), 7.18 (s, 1H), 7.05(d, 1H), 3.91(d, 2H) |
| I-32 | 337.2 | DMSO-d6: 8.70(d, 2H), 8.10(d, 1H), 7.97(t, 1H), 7.90(d, 2H), 7.69(s, 1H), 7.22(s, 1H), 7.05 (d, 1H), 3.90(d, 2H) |
| I-33 | 287.2 | DMSO-d6: 8.02(d, 1H), 7.96(t, 1H), 7.67(t, 1H), 7.60(m, 1H), 7.50(s, 1H), 7.40(m, 2H), 7.15(s, 1H), 7.05(d, 1H), 3.77(d, 2H) |
| I-34 | 287.2 | DMSO-d6: 8.35(d, 1H), 8.21(d, 1H), 8.05(d, 1H), 7.89(t, 1H), 7.61(m, 2H), 7.35(t, 1H), 7.20 (s, 1H), 7.05(d, 1H), 3.90(d, 2H) |
| I-35 | 338.1 | DMSO-d6: 8.78(s, 1H), 8.70(d, 1H), 8.08(m, 2H), 7.89(d, 1H), 7.80(m, 1H), 7.05(d, 1H), 4.05(d, 2H) |
| I-36 | 277.2 | DMSO-d6: 9.13(s, 1H), 8.78(d, 1H), 8.05(d, 1H), 7.95(m, 2H), 7.81(t, 1H), 6.85(d, 1H), 2.70 (m, 1H), 0.85(m, 2H), 0.50(m, 2H) |
| I-37 | 294.2 | DMSO-d6: 8.65(d, 2H), 8.10(d, 1H), 7.95(m, 3H), 7.67(s, 1H), 7.20(s, 1H), 7.05(d, 1H), 3.90 (d, 2H) |
| I-38 | 299.2 | DMSO-d6: 8.40(d, 2H), 8.00(d, 1H), 7.78(t, 1H), 7.62(s, 1H), 7.20(s, 1H), 7.09(d, 2H), 6.96 (d, 1H), 3.87(d, 2H), 3.84(s, 3H) |
| I-39 | 299.2 | DMSO-d6: 8.08(d, 1H), 8.03(d, 1H), 8.01(m, 1H), 7.80(t, 1H), 7.59(m, 1H), 7.46(t, 1H), 7.18 (s, 1H), 7.07(d, 1H), 7.01(d, 1H), 3.91(d, 2H), 3.87(s, 3H) |
| I-40 | 294.2 | DMSO-d6: 8.80(d, 1H), 8.72(s, 1H), 8.08(d, 1H), 7.98(d, 1H), 7.95(t, 1H), 7.76 m, 1H), 7.61 s, 1H), 7.15(s, 1H), 7.05(d, 1H), 3.92(d, 2H) |
| I-42 | 242 | DMSO-d6: 7.60(d, 1H), 7.49(d, 2H), 6.95(t, 2H), 6.35(d, 1H), 6.30(t, 1H), 3.93(s, 3H) |
| I-43 | 319.97 | DMSO-d6: 9.50(s, 1H), 8.05(d, 1H), 7.75(d, 2H), 7.65(m, 2H), 7.55(m, 3H), 7.35(t, 2H), 6.95(t, 1H), 6.69(t, 1H) |
| I-44 | 304.02 | DMSO-d6: 9.17(s, 1H), 8.26(d, 1H), 7.66(d, 2H), 7.46(t, 2H), 7.33(d, 2H), 7.28(m, 3H), 7.02 (d, 1H), 6.92(t, 1H) |
| I-45 | 260.01 | MeOH-d4: 7.90(d, 1H), 7.68(m, 2H), 7.07(m, 2H), 6.89(d, 1H), 4.1(s, 3H) |
| I-46 | 260 | MeOH-d4: 7.90(d, 1H), 7.58(d, 1H), 7.45(d, 1H), 7.30(m, 1H), 6.90(d, 1H), 6.70(t, 1H), 4.1 (s, 3H) |
| I-47 | 260.01 | DMSO-d6: 8.50(s, 1H), 8.13(d, 1H), 7.85(t, 1H), 7.25(m, 1H), 7.16(t, 1H), 7.01(m, 1H), 6.93(d, 1H), 3.97(s, 3H) |
| I-48 | 337.97 | DMSO-d6: 9.60(s, 1H), 8.05(d, 1H), 7.85(m, 2H), 7.67(m, 2H), 7.52(m, 3H), 7.18(t, 2H), 6.68(d, 1H) |
| I-49 | 337.95 | DMSO-d6: 9.83(s, 1H), 8.06(d, 1H), 7.73(d, 1H), 7.67(m, 2H), 7.60(d, 1H), 7.51(m, 3H), 7.34(m, 1H), 6.75(t, 1H), 6.70(d, 1H) |
| I-50 | 337.97 | DMSO-d6: 8.44(s, 1H), 8.10(d, 1H), 7.80(t, 1H), 7.65(d, 2H), 7.50(m, 3H), 7.27(t, 1H), 7.15 (t, 1H), 7.03(m, 1H), 6.94(d, 1H) |
| I-51 | 309.99 | DMSO-d6: 9.59(s, 1H), 8.15(d, 1H), 7.95(d, 2H), 7.70(d, 2H), 6.95(d, 1H), 4.05(s, 3H) |
| I-52 | 309.99 | DMSO-d6: 9.50(s, 1H), 8.13(s, 1H), 8.15(d, 1H), 8.08(d, 1H), 7.58(t, 1H), 7.29(d, 1H), 6.95 (d, 1H), 4.10(s, 3H) |
| I-53 | 309.98 | DMSO-d6: 8.19(d, 1H), 8.02(s, 1H), 7.91(d, 1H), 7.71(d, 1H), 7.65(t, 1H), 7.21(t, 1H), 7.00 (d, 1H), 3.90(s, 3H) |
| I-54 | 322.02 | DMSO-d6: 9.30(s, 1H), 8.27(d, 1H), 7.69(m, 2H), 7.45(m, 2H), 7.33(d, 2H), 7.27(t, 1H), 7.15 (t, 2H), 7.05(d, 1H) |
| I-55 | 322.01 | DMSO-d6: 9.55(s, 1H), 8.29(d, 1H), 7.59(d, 1H), 7.451(m, 3H), 7.35-7.25(m, 4H), 7.05(d, 1H), 6.72(t, 1H) |
| I-56 | 322.04 | DMSO-d6: 8.51(s, 1H), 8.31(d, 1H), 7.59(t, 1H), 7.41(t, 2H), 7.33-7.11(m, 6H), 7.01(m, 1H) |
| I-57 | 388.05 | DMSO-d6: 10.07(s, 1H), 8.10(d, 1H), 7.92(d, 2H), 7.67(m, 4H), 7.50(m, 3H), 6.75(d, 1H) |
| I-58 | 388.04 | DMSO-d6: 10.5(s, 1H), 8.3(s, 1H), 8.1(d, 1H), 8.05(d, 1H), 7.67(m, 2H), 7.58-7.49(m, 4H), 7.29(d, 1H), 6.71(d, 1H) |
| I-59 | 388.05 | DMSO-d6: 8.17(d, 1H), 8.00(d, 1H), 7.82(s, 1H), 7.68(d, 1H), 7.63(m, 3H), 7.53(m, 1H), 7.47(d, 2H), 7.19(t, 1H), 7.14(d, 1H) |
| I-60 | 350 | DMSO-d6: 9.26(s, 1H), 8.02(d, 1H), 7.75(d, 2H), 7.66(m, 2H), 7.53(m, 3H), 6.91(d, 2H), 3.75(s, 3H) |

-continued

| Compound Number | MSpos | NMR |
|---|---|---|
| I-63 | 334.02 | DMSO-d6: 9.05(s, 1H), 8.25(d, 1H), 7.60(d, 2H), 7.50(m, 2H), 7.35(m, 3H), 7.05(d, 1H), 6.95(m, 2H), 3.79(s, 3H) |
| I-61 | 349.99 | DMSO-d6: 9.55(s, 1H), 8.05(d, 1H), 7.70(m, 2H), 7.51(m, 3H), 7.45(s, 1H), 7.35(d, 1H), 7.24(t, 1H), 6.73(d, 1H), 6.57(d, 1H), 3.75(s, 3H) |
| I-64 | 334.03 | DMSO-d6: 9.20(s, 1H), 8.25(d, 1H), 7.48(m, 2H), 7.35-7.18(m, 6H), 7.05(d, 1H), 6.52(d, 1H), 3.75(s, 3H) |
| I-62 | 350 | DMSO-d6: 8.20(m, 1H), 8.15(d, 1H), 7.75(d, 2H), 7.68-7.58(m, 4H), 7.15(d, 1H), 7.05(m, 1H), 7.00(m, 2H), 3.85(s, 3H) |
| I-66 | 272.03 | DMSO-d6: 8.80(s, 1H), 8.05(d, 1H), 7.73(d, 2H), 6.92(d, 2H), 6.87(d, 1H), 4.05(s, 3H), 3.75(s, 3H) |
| I-67 | 272.04 | DMSO-d6: 9.00(s, 1H), 8.10(d, 1H), 7.47(s, 1H), 7.37(d, 1H), 7.22(t, 1H), 6.90(d, 1H), 6.55(d, 1H), 4.05(s, 3H), 3.86(s, 3H) |
| I-68 | 272.04 | DMSO-d6: 8.21(d, 1H), 7.65(s, 1H), 7.10(d, 1H), 7.05-6.95(m, 3H), 4.05(s, 3H), 3.95(s, 3H) |
| I-69 | 344.9 | DMSO-d6: 10.2(s, 1H), 8.12(d, 1H), 7.90(d, 2H), 7.75(d, 2H), 7.65(d, 2H), 7.55(m, 3H), 6.75(d, 1H) |
| I-70 | 328.04 | DMSO-d6: 9.65(d, 2H), 8.01(d, 1H), 7.75(m, 4H), 7.65(d, 2H), 7.19(t, 2H), 7.00(m, 2H) |
| I-71 | 344.9 | DMSO-d6: 10.05(s, 1H), 8.25(s, 1H), 8.11(d, 1H), 8.06(d, 1H), 7.67(d, 2H), 7.50(m, 4H), 7.40(m, 1H), 6.75(d, 1H) |
| I-72 | 329 | DMSO-d6: 9.71(s, 1H), 8.28(d, 1H), 8.05(s, 1H), 7.9(d, 1H), 7.45-7.22(m, 7H), 7.09(d, 1H) |
| I-73 | 267.04 | DMSO-d6: 9.70(s, 1H), 8.15(d, 1H), 7.87(d, 2H), 7.75(d, 2H), 6.96(d, 1H), 4.05(s, 3H) |
| I-74 | 267.04 | DMSO-d6: 9.52(s, 1H), 8.25(d, 1H), 8.15(d, 1H), 8.05(d, 1H), 7.55(t, 1H), 7.39(d, 1H), 6.96(d, 1H), 4.05(s, 3H) |
| I-75 | 292 | DMSO-d6: 9.45(s, 1H), 7.84(d, 1H), 7.80-7.70(m, 4H), 7.65(d, 1H), 6.72(d, 1H), 2.80(m, 1H), 0.70(m, 2H), 0.50(m, 2H) |
| I-76 | 292 | DMSO-d6: 9.19(s, 1H), 8.12(s, 1H), 7.99(d, 1H), 7.82(d, 1H), 7.53(m, 2H), 7.35(m, 2H), 6.68(d, 1H), 2.82(m, 1H), 0.79(m, 2H), 0.51(m, 2H) |
| I-77 | 285 | MeOH-d4: 7.89(d, 1H), 7.52(d, 1H), 7.45(d, 1H), 7.38(m, 1H), 7.18(d, 1H), 6.83(t, 1H), 2.94(m, 1H), 0.90(m, 2H), 0.62(m, 2H) |
| I-78 | 285 | MeOH-d4: 7.81(d, 1H), 7.62(m, 2H), 7.15(m, 3H), 2.90(m, 1H), 0.88(m, 2H), 0.60(m, 2H) |
| I-79 | 285 | MeOH-d4: 7.81(m, 1H), 7.26(m, 3H), 7.05(d, 1H), 2.82(m, 1H), 0.85(m, 2H), 0.60(m, 2H) |
| I-80 | 335 | MeOH-d4: 7.85(m, 3H), 7.66(d, 2H), 7.12(d, 1H), 2.90(m, 1H), 0.90(m, 2H), 0.60(m, 2H) |
| I-81 | 335 | MeOH-d4: 8.07(s, 1H), 7.90(m, 2H), 7.56(t, 1H), 7.40(d, 1H), 7.18(d, 1H), 2.93(m, 1H), 0.90(m, 2H), 0.61(m, 2H) |
| I-82 | 297 | MeOH-d4: 7.83(d, 1H), 7.33-7.10(m, 4H), 6.74(d, 1H), 3.81(s, 3H), 2.90(m, 1H), 0.90(m, 2H), 0.64(m, 2H) |
| I-83 | 297 | MeOH-d4: 7.86(d, 1H), 7.80(d, 1H), 7.19(m, 1H), 7.15(d, 1H), 7.05(m, 2H), 3.95(s, 3H), 2.80(m, 1H), 0.89(m, 2H), 0.65(m, 2H) |
| I-84 | 302 | DMSO-d6: 8.15(d, 1H), 7.95(s, 1H), 7.65(s, 1H), 7.02(d, 1H), 6.95(d, 1H), 6.54(d, 1H), 4.05(s, 3H), 3.90(s, 3H), 3.80(s, 3H) |
| I-85 | 302 | DMSO-d6: 8.40(s, 1H), 8.16(d, 1H), 7.81(d, 1H), 7.05(d, 1H), 6.75(s, 1H), 6.60(d, 1H), 4.05(s, 3H), 3.90(s, 3H), 3.80(s, 3H) |
| I-86 | 332 | DMSO-d6: 8.90(s, 1H), 8.10(d, 1H), 7.30(s, 2H), 6.90(d, 1H), 4.10(s, 3H), 3.83(s, 6H), 3.67(s, 3H) |

Example 2

Inhibition of PIM-1

Compounds were screened for their ability to inhibit PIM-1 using a standard coupled enzyme assay (Fox et al (1998) *Protein Sci* 7, 2249). Reactions were carried out in 100 mM HEPES pH 7.5, 10 mM $MgCl_2$, 25 mM NaCl, 1 mM DTT, 20 µg/ml BSA and 1.5% DMSO. Final substrate concentrations in the assay were 120 µM ATP (Sigma chemicals) and 200 µM peptide (American Peptide, Sunnyvale, Calif.). Assays were carried out at 30° C. and 50 nM PIM-1. Final concentrations of the components of the coupled enzyme system were 2.5 mM phosphoenolpyruvate, 350 µM NADH, 30 µg/ml pyruvate kinase and 10 µg/ml lactate dehydrogenase.

An assay stock buffer solution was prepared containing all of the reagents listed above, with the exception of PIM-1, DTT, BSA and the test compound of interest. 56 µl of the test reaction was placed in a 384 well plate followed by addition of 1 µl of 2 mM DMSO stock containing the test compound (final compound concentration 30 µM). The plate was pre-incubated for ~10 minutes at 30° C. and the reaction initiated by addition of 10 µl of enzyme in DTT and BSA (final concentrations: 50 nM PIM-1, 1 mM DTT, and 20 µg/ml BSA). Rates of reaction were obtained using a BioRad Ultramark plate reader (Hercules, Calif.) over a 5 minute read time at 30° C. Compounds showing >50% inhibition versus standard wells containing DMSO, but no compound, were titrated and IC50's determined using a similar protocol.

Compounds of the invention were shown to inhibit PIM-1 using the assay methods described above. In certain embodiments, the following compounds were shown to have $IC_{50}$ or $K_i$ values less than 1.0 µM for PIM-1: I-5, I-18, I-20, I-21, I-24, I-25, I-26, and I-28.

Example 3

Inhibition of GSK-3

Compounds were screened for their ability to inhibit GSK-3β (AA 1-420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of interest. The assay stock buffer solution (175 µl) was incubated in a 96 well plate with 5 µl of the test compound of interest at final concentrations spanning 0.002 µM to 30 µM at 30° C. for 10 min. Typically, a 12 point titration was conducted by preparing serial dilutions (from 10 mM compound stocks) with DMSO of the test compounds in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The $K_i$ values were determined from the rate data as a function of inhibitor concentration.

Compounds of the invention were shown to inhibit GSK-3 using the assay methods described above. In certain embodiments, the following compounds were shown to have $K_i$ values less than 2.0 µM for GSK-3: I-18, I-21, I-37, I-38, I-39, I-40, I-62, I-66, I-85, and I-86.

Example 4

Inhibition of CDK-2

Compounds were screened for their ability to inhibit CDK-2/Cyclin A using a standard coupled enzyme assay (Fox et al (1998) *Protein Sci* 7, 2249). Reactions were carried out in 100 mM HEPES pH 7.5, 10 mM $MgCl_2$, 25 mM NaCl, 1 mM DTT and 1.5% DMSO. Final substrate concentrations in the assay were 100 µM ATP (Sigma chemicals) and 100 µM peptide (American Peptide, Sunnyvale, Calif.). Assays were carried out at 30° C. and 25 nM CDK-2/Cyclin A. Final concentrations of the components of the coupled enzyme system were 2.5 mM phosphoenolpyruvate, 350 µM NADH, 30 µg/ml pyruvate kinase and 10 µg/ml lactate dehydrogenase.

An assay stock buffer solution was prepared containing all of the reagents listed above, with the exception of CDK-2/Cyclin A, DTT and the test compound of interest. 56 µl of the test reaction was placed in a 384 well plate followed by addition of 1 µl of 2 mM DMSO stock containing the test compound (final compound concentration 30 µM). The plate was preincubated for ~10 minutes at 30° C. and the reaction initiated by addition of 10 µl of enzyme (final concentration 25 nM). Rates of reaction were obtained using a BioRad Ultramark plate reader (Hercules, Calif.) over a 5 minute read time at 30° C. $K_i$ values were determined according to standard methods.

Compounds of the invention were shown to inhibit CDK-2 using the assay methods described above. In certain embodiments, the following compounds were shown to have $K_i$ values less than 2.0 µM for CDK-2: I-68 and I-73.

Example 5

Inhibition of SRC

The compounds are evaluated as inhibitors of human Src kinase using either a radioactivity-based assay or spectrophotometric assay.

Src Inhibition Assay A: Radioactivity-based Assay

The compounds are assayed as inhibitors of full length recombinant human Src kinase (from Upstate Biotechnology, cat. no. 14-117) expressed and purified from baculo viral cells. Src kinase activity is monitored by following the incorporation of $^{33}P$ from ATP into the tyrosine of a random poly Glu-Tyr polymer substrate of composition, Glu:Tyr=4:1 (Sigma, cat. no. P-0275). The following are the final concentrations of the assay components: 0.05 M HEPES, pH 7.6, 10 mM $MgCl_2$, 2 mM DTT, 0.25 mg/ml BSA, 10 µM ATP (1-2 µCi $^{33}P$-ATP per reaction), 5 mg/ml poly Glu-Tyr, and 1-2 units of recombinant human Src kinase. In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with $^{33}P$-ATP. After 20 min of reaction, the reactions are quenched with 150 µl of 10% trichloroacetic acid (TCA) containing 20 mM $Na_3PO_4$. The quenched samples are then transferred to a 96-well filter plate (Whatman, UNI-Filter GF/F Glass Fiber Filter, cat no. 7700-3310) installed on a filter plate vacuum manifold. Filter plates are washed four times with 10% TCA containing 20 mM $Na_3PO_4$ and then 4 times with methanol. 200 µl of scintillation fluid is then added to each well. The plates were sealed and the amount of radioactivity associated with the filters is quantified on a TopCount scintillation counter. The radioactivity incorporated is plotted as a function of the inhibitor concentration. The data is fitted to a competitive inhibition kinetics model to get the $K_i$ for the compound.

Src Inhibition Assay B: Spectrophotometric Assay

The ADP produced from ATP by the human recombinant Src kinase-catalyzed phosphorylation of poly Glu-Tyr substrate is quantified using a coupled enzyme assay (Fox et al (1998) *Protein Sci* 7, 2249). In this assay one molecule of NADH is oxidised to NAD for every molecule of ADP produced in the kinase reaction. The disappearance of NADH is conveniently followed at 340 nm.

The following are the final concentrations of the assay components: 0.025 M HEPES, pH 7.6, 10 mM $MgCl_2$, 2 mM DTT, 0.25 mg/ml poly Glu-Tyr, and 25 nM of recombinant human Src kinase. Final concentrations of the components of the coupled enzyme system are 2.5 mM phosphoenolpyruvate, 200 µM NADH, 30 µg/ml pyruvate kinase and 10 µg/ml lactate dehydrogenase.

In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with 100 µM ATP. The absorbance change at 340 nm with time, the rate of the reaction, is monitored on a molecular devices plate reader. The data of rate as a function of the inhibitor concentration is fitted to competitive inhibition kinetics model to get the $K_i$ for the compound.

Compounds of the invention were shown to inhibit SRC using the assay methods described above. In certain embodiments, the following compounds were shown to have $K_i$ values less than 5.0 µM for SRC: I-25, I-26, I-28, and I-29.

The invention claimed is:
1. A compound of formula (I):

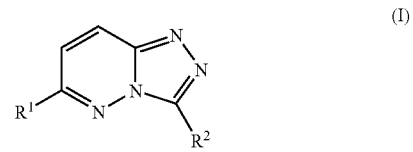

or a pharmaceutically acceptable salt thereof,
wherein $R^1$ is $NR^3R^4$; wherein $R^4$ is hydrogen or optionally substituted $C_{1-4}$alkyl and $R^3$ is an optionally substituted aryl, heteroaryl, cycloaliphatic, or heterocycloaliphatic group each occurrence of R is independently selected from hydrogen or an optionally substituted $C_{1-6}$ aliphatic group, and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together, or two occurrences of R' on the same substituent or different substituents, taken together, form a 5-8 membered heterocyclyl or heteroaryl ring having 1-3 heteroatoms independently selected from nitrogen, oxygen, or sulfur; and
R² is -(T)ₙAr¹, wherein T is NR; n is 0 or 1; Ar¹ is an optionally substituted group selected from
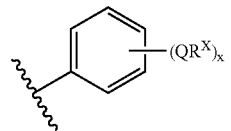 a
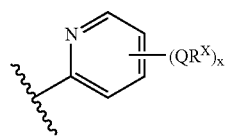 b
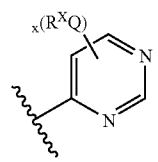 c
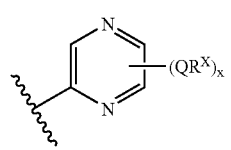 d
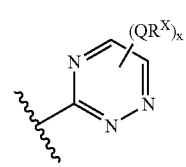 e
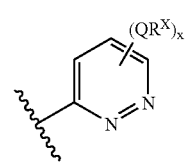 f
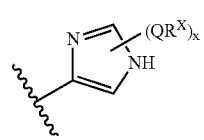 g
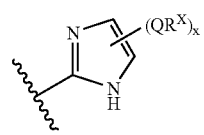 h
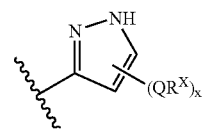 i
-continued
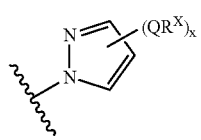 j
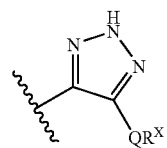 k
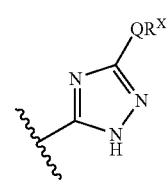 l
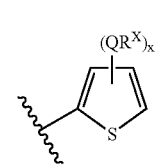 m
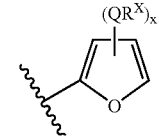 n
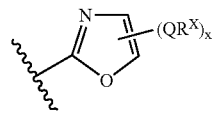 o
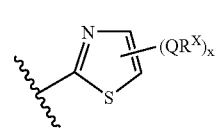 p
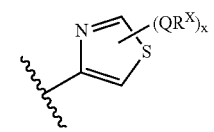 q
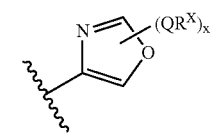 r
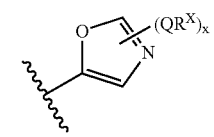 s
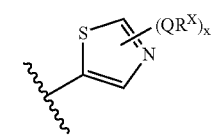 t

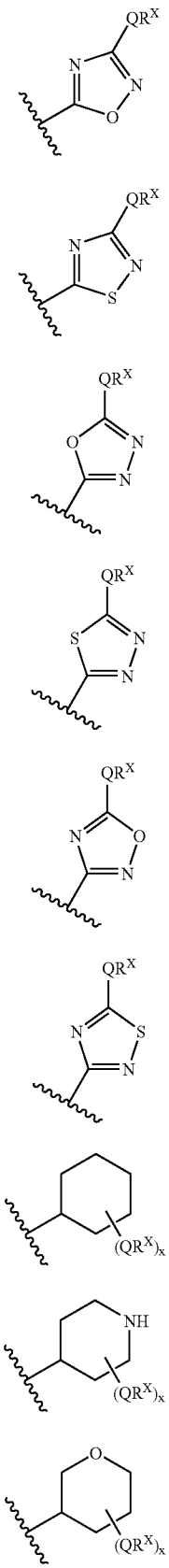
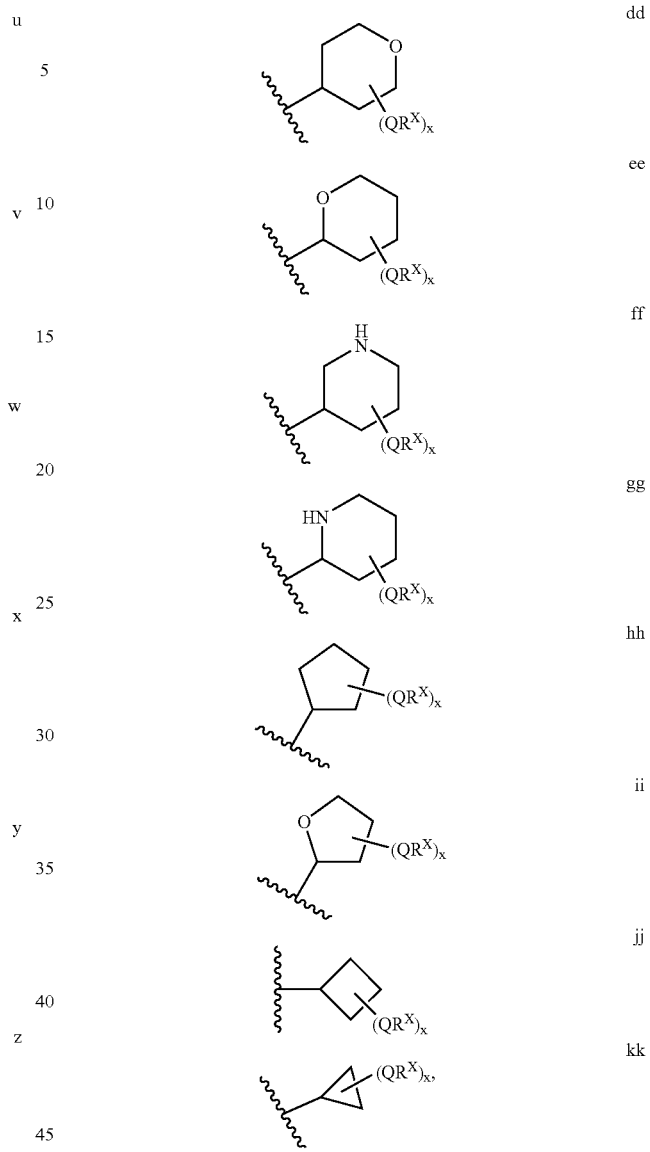

wherein any substitutable carbon or nitrogen atom is optionally substituted and wherein x is 0-5, Q is a bond or is a $C_1$-$C_6$ alkylidene chair wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';

provided that:
1) $R^2$ is not nitro substituted pyrazolyl, nitro substituted furyl, or nitro substituted thiophene;
2) when $R^1$ is —NH(cyclopropyl), then $R^2$ is not phenyl substituted with one occurrence of $CF_3$ in the para position.

2. The compound of claim 1, wherein n is 1, T is NR, and R² is —NRAr¹, and compounds have the general formula IIA:

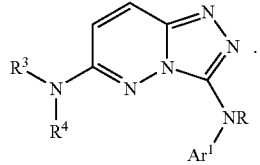

IIA

3. The compound of claim 1, wherein m is 0, and R² is —Ar¹, and compounds have the general formula IIB:

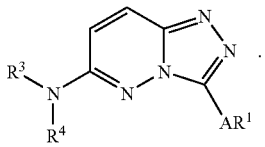

IIB

4. The compound of claim 1, wherein R⁴ is hydrogen or optionally substituted $C_{1-4}$alkyl and R³ is an optionally substituted 5- or 6-membered aryl or heteroaryl group.

5. The compound of claim 1, wherein R⁴ is hydrogen or optionally substituted $C_{1-4}$alkyl and R³ is an optionally substituted 3-7-membered cycloaliphatic or heterocycloaliphatic group.

6. The compound of claim 1, wherein R⁴ is hydrogen or optionally substituted $C_{1-4}$alkyl, and R³ is an optionally substituted cyclic group selected from:

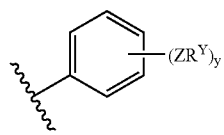

i

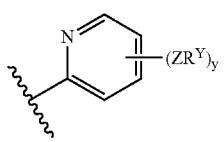

ii

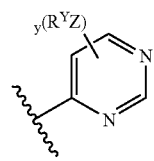

iii

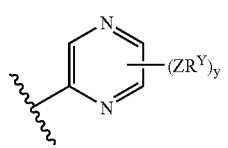

iv

-continued

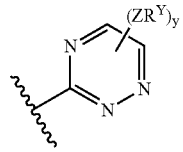

v

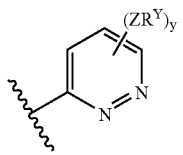

vi

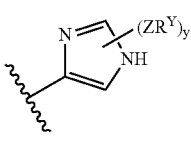

vii

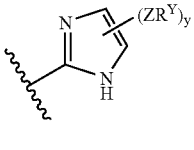

viii

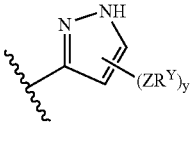

ix

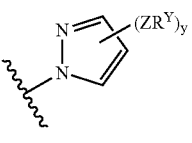

x

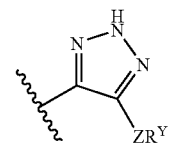

xi

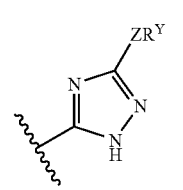

xii

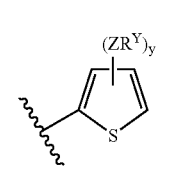

xiii

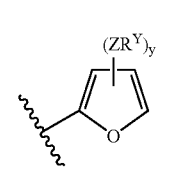

xiv

-continued

| | |
|---|---|
| xv | xxv |
| xvi | xxvi |
| xvii | xxvii |
| xviii | xxviii |
| xix | xxix |
| xx | xxx |
| xxi | xxxi |
| xxii | xxxii |
| xxiii | xxxiii |
| xxiv | xxxiv |

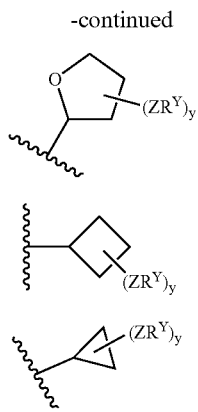

wherein any substitutable carbon or nitrogen atom is optionally substituted and wherein y is 0-5, Z is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^Y$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, C(O)C(O)R', or $C(O)CH_2C(O)R'$.

7. The compound of claim 6, wherein one of $R^3$ is selected from one of the following groups:

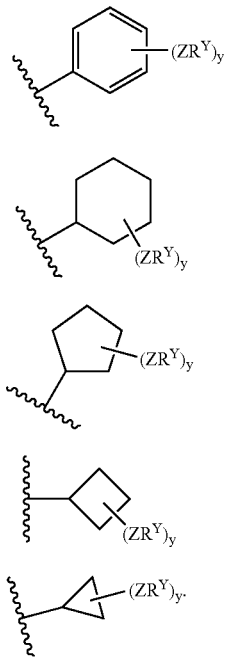

8. The compound of claim 6, wherein y is 0-3 and thus $R^3$ is substituted with 0-3 occurrences of $ZR^Y$.

9. The compound of claim 6, wherein y is 1 or 2.

10. The compound of claim 6, wherein y is 0 and $R^3$ is unsubstituted.

11. The compound of claim 6, wherein each occurrence of $ZR^Y$ is independently halogen, CN, $NO_2$, or an optionally substituted group selected from $C_{1-4}$alkyl, aryl, aralkyl, $-N(R')_2$, $CH_2N(R')_2$, $-OR'$, $CH_2OR'$, $-SR'$, $CH_2SR'$, COOR', or $-S(O)_2N(R')_2$.

12. The compound of claim 6, wherein each occurrence of $ZR^Y$ is independently Cl, Br, F, CN, $CF_3$, COOH, $-N(CH_3)_2$, $-OH$, $CH_2OH$, or an optionally substituted group selected from $C_{1-4}$alkoxy, $C_{1-4}$alkyl, phenyl, phenyloxy, benzyl, or benzyloxy.

13. The compound of claim 1, wherein x is 0-3 and $R^2$ is substituted with 0-3 occurrences of $QR^X$.

14. The compound of claim 1, wherein x is 1 or 2.

15. The compound of claim 1, wherein x is 0.

16. The compound of claim 1, wherein each occurrence of $QR^X$ is independently halogen, CN, $NO_2$, or an optionally substituted group selected from $C_{1-4}$alkyl, aryl, aralkyl, $-N(R')_2$, $CH_2N(R')_2$, $-OR'$, $CH_2OR'$, $-SR'$, $CH_2SR'$, COOR', or $-S(O)_2N(R')_2$.

17. The compound of claim 1, wherein each occurrence of $QR^X$ is independently Cl, Br, F, CN, $CF_3$, COOH, $-N(CH_3)_2$, $-OH$, $CH_2OH$, or an optionally substituted group selected from $C_{1-4}$alkoxy, $C_{1-4}$alkyl, phenyl, phenyloxy, benzyl, or benzyloxy.

18. The compound of claim 1, wherein $R^4$ is hydrogen or $C_{1-4}$alkyl; $R^3$ is optionally substituted phenyl; and $R^2$ is $-NRAr^1$, and compounds have one of the following formulas:

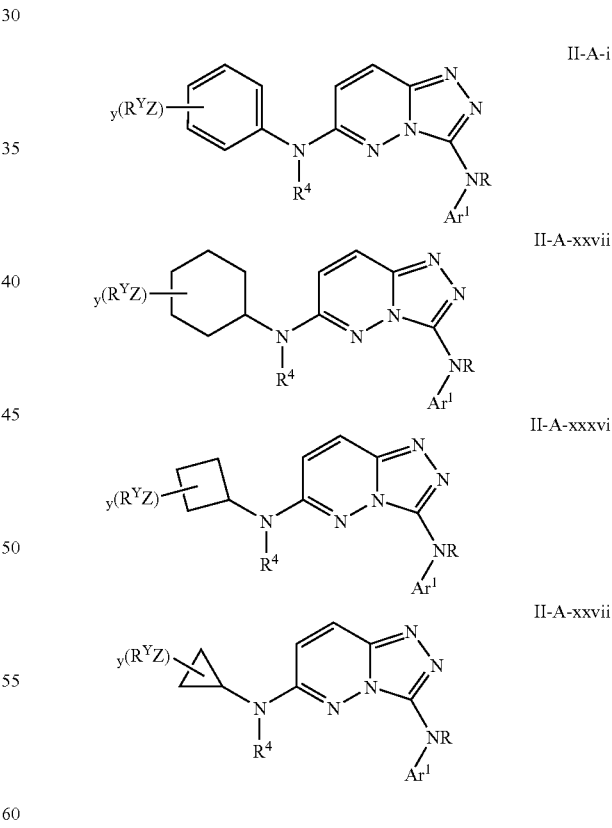

wherein y is 0-5, Z is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^Y$ is independently selected from R', halogen, $NO_2$, CN, OR', SR', $N(R')_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'.

19. The compound of claim 1, wherein R$^2$ is Ar$^1$, and compounds have one of the following formulas:

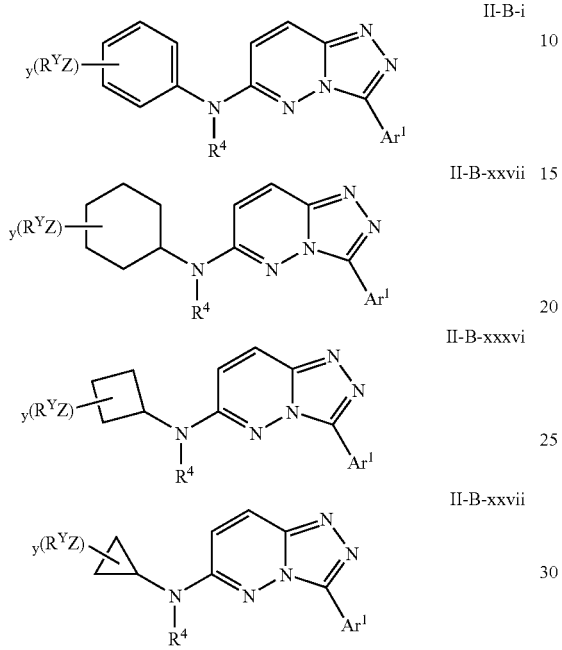

wherein y is 0-5, Z is a bond or is a C$_1$-C$_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, 502, NRSO$_2$, SO$_2$NR, NRSO$_2$NR, O, S, or NR; and each occurrence of R$^Y$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'.

20. The compound of claim 1, wherein R$^2$ is NRAr$^1$ and Ar$^1$ is optionally substituted phenyl, and compounds have one of the following formula:

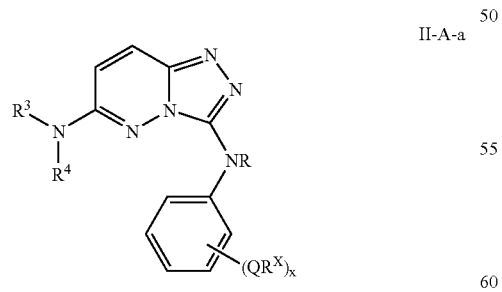

wherein x is 0-5, Q is a bond or is a C$_1$-C$_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^X$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SC$_2$R', NR'SO$_2$N(R')$_2$, C(O)C(O)R', or C(O)CH$_2$C(O)R'.

21. The compound of claim 1, wherein R$^2$ is —Ar$^1$, wherein Ar$^1$ is optionally substituted phenyl, and compounds have formula:

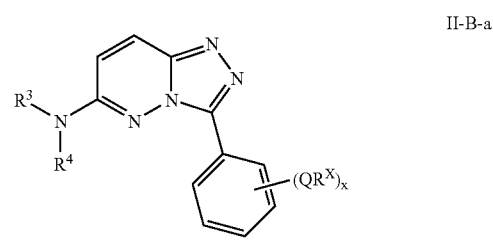

wherein x is 0-5, Q is a bond or is a C$_1$-C$_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^X$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'.

22. The compound of claim 20 or 21, wherein:

(a) R$^4$ is hydrogen or C$_{1-4}$alkyl;

(b) when n is 1, and T is NR, R is hydrogen or C$_{1-4}$alkyl;

(c) R$^3$ is a group selected from:

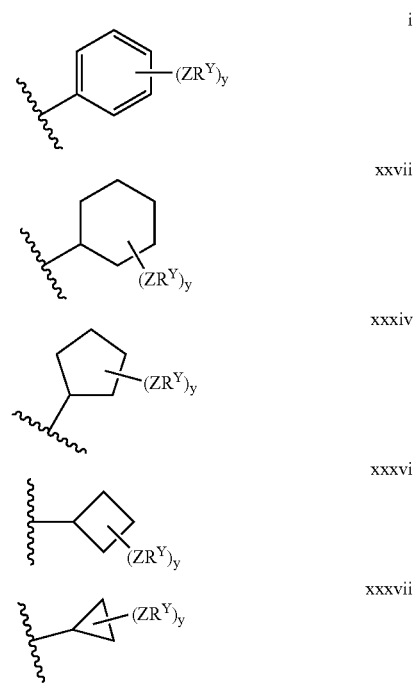

wherein y is 0-3, Z is a bond or is a C$_1$-C$_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^Y$ is independently selected from R', halogen, NO₂, CN, OR', SR', N(R')₂, NR'C(O)R', NR'C(O)N(R')₂, NR'CO₂R', C(O)R', CO₂R', OC(O)R', C(O)N(R')₂, OC(O)N(R')₂, SOR', SO₂R', SO₂N(R')₂, NR'SO₂R', NR'SO₂N(R')₂, C(O)C(O)R', or C(O)CH₂C(O)R'; and (d) x is 0-3, Q is a bond or is a $C_1$-$C_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^X$ is independently selected from R', halogen, NO₂, CN, OR', SR', N(R')₂, NR'C(O)R', NR'C(O)N(R')₂, NR'CO₂R', C(O)R', CO₂R', OC(O)R', C(O)N(R')₂, OC(O)N(R')₂, SOR', SO₂R', SO₂N(R')₂, NR'SO₂R', NR'SO₂N(R')₂, C(O)C(O)R', or C(O)CH₂C(O)R'.

23. The compound of claim 22, wherein y is 0-3 and $R^3$ is substituted with 0-3 occurrences of $ZR^Y$, and x is 0-3 and $R^2$ is substituted with 0-3 occurrences of $QR^X$.

24. The compound of claim 22, wherein y is 0, 1, or 2; and x is 0, 1, or 2.

25. The compound of claim 22, wherein y is 0; and x is 0, 1, or 2.

26. The compound of claim 22, wherein x is 0; and y is 0, 1, or 2.

27. The compound of claim 22, wherein each occurrence of $ZR^Y$ is independently halogen, CN, NO₂, or an optionally substituted group selected from $C_{1-4}$alkyl, aryl, aralkyl, —N(R')₂, CH₂N(R')₂, —OR', CH₂OR', —SR', CH₂SR', COOR', or —S(O)₂N(R')₂; and each occurrence of $QR^X$ is independently halogen, CN, NO₂, or an optionally substituted group selected from $C_{1-4}$alkyl, aryl, aralkyl, —N(R')₂, CH₂N(R')₂, —OR', CH₂OR', —SR', CH₂SR', COOR', or —S(O)₂N(R')₂.

28. The compound of claim 22, wherein each occurrence of $ZR^Y$ is independently Cl, Br, F, CN, CF₃, COOH, —N(CH₃)₂, —OH, CH₂OH, or an optionally substituted group selected from $C_{1-4}$alkoxy, $C_{1-4}$alkyl, phenyl, phenyloxy, benzyl, or benzyloxy; and each occurrence of $QR^X$ is independently Cl, Br, F, CN, CF₃, COOH, —N(CH₃)₂, —OH, CH₂OH, or an optionally substituted group selected from $C_{1-4}$alkoxy, $C_{1-4}$alkyl, phenyl, phenyloxy, benzyl, or benzyloxy.

29. The compound of claim 1, wherein $R^3$ is an optionally substituted group selected from phenyl, cyclohexyl, cyclobutyl or cyclopropyl, and $R^2$ is NRAr¹, wherein R is hydrogen or $C_{1-4}$alkyl, and Ar¹ is optionally substituted phenyl, and compounds have one of the following formulas:

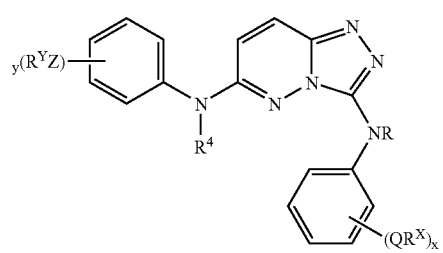

II-A-i-a

-continued

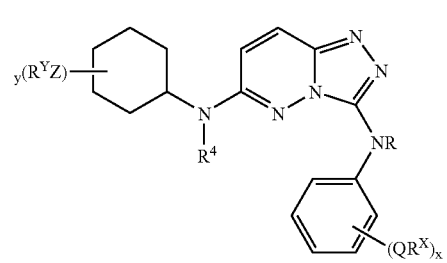

II-A-xxvii-a

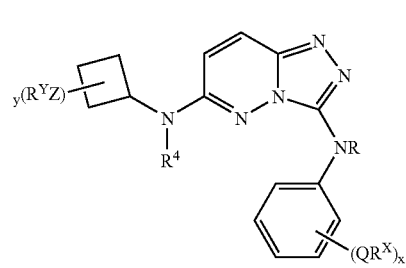

II-A-xxxvi-a

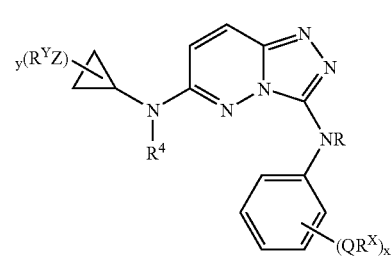

II-A-xxvii-a wherein x is 0-5, Q is a bond or is a $C_1$-$C_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^X$ is independently selected from R', halogen, NO₂, CN, OR', SR', N(R')₂, NR'C(O)R', NR'C(O)N(R')₂, NR'CO₂R', C(O)R', CO₂R', OC(O)R', C(O)N(R')₂, OC(O)N(R')₂, SOR', SO₂R', SO₂N(R')₂, NR'SO₂R', NR'SO₂N(R')₂, C(O)C(O)R', or C(O)CH₂C(O)R'; and wherein y is 0-5, Z is a bond or is a $C_1$-$C_6$ alkylidene chain wherein up to two non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^Y$ is independently selected from R', halogen, NO₂, CN, OR', SR', N(R')₂, NR'C(O)R', NR'C(O)N(R')₂, NR'CO₂R', C(O)R', CO₂R', OC(O)R', C(O)N(R')₂, OC(O)N(R')₂, SOR', SO₂R', SO₂N(R')₂, NR'SO₂R', NR'SO₂N(R')₂, C(O)C(O)R', or C(O)CH₂C(O)R'.

30. The compound of claim 1, wherein $R^3$ is an optionally substituted group selected from phenyl, cyclohexyl, cyclobutyl or cyclopropyl, and $R^2$ is Ar¹, wherein Ar¹ is optionally substituted phenyl, and compounds have one of the following formulas:

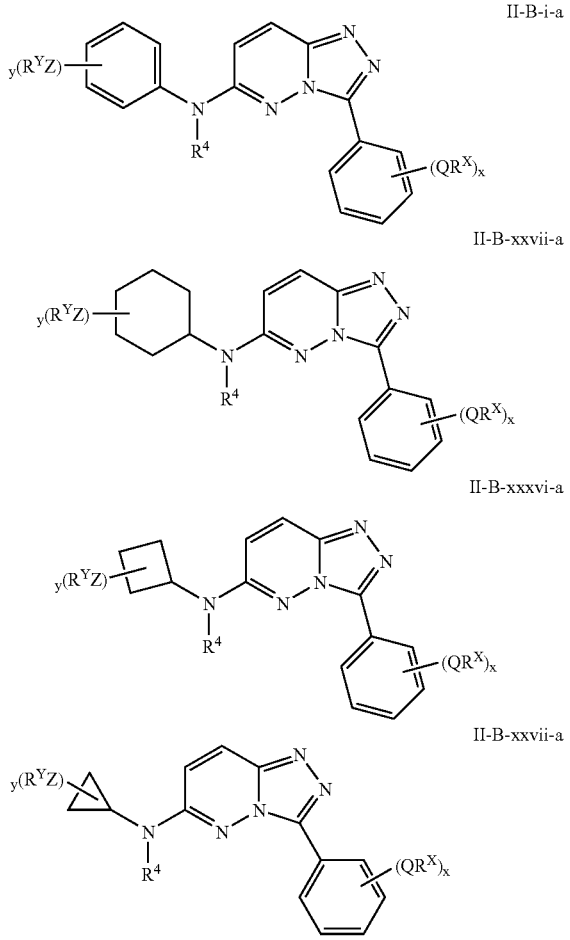

33. The compound of claim 29 or 30, wherein y is 0; and x is 0, 1, or 2.

34. The compound of claim 29 or 30, wherein x is 0; and y is 0, 1, or 2.

35. The compound of claim 29 or 30, wherein each occurrence of $ZR^Y$ is independently halogen, CN, $NO_2$, or an optionally substituted group selected from $C_{1-4}$alkyl, aryl, aralkyl, —N(R')$_2$, CH$_2$N(R')$_2$, —OR', CH$_2$OR', —SR', CH$_2$SR', COOR', or —S(O)$_2$N(R')$_2$; and each occurrence of $QR^X$ is independently halogen, CN, $NO_2$, or an optionally substituted group selected from $C_{1-4}$alkyl, aryl, aralkyl, —N(R')$_2$, CH$_2$N(R')$_2$, —OR', CH$_2$OR', —SR', CH$_2$SR', COOR', or —S(O)$_2$N(R')$_2$.

36. The compound of claim 29 or 30, wherein each occurrence of $ZR^Y$ is independently Cl, Br, F, CN, $CF_3$, COOH, —N(CH$_3$)$_2$, —OH, CH$_2$OH, or an optionally substituted group selected from $C_{1-4}$alkoxy, $C_{1-4}$alkyl, phenyl, phenyloxy, benzyl, or benzyloxy; and each occurrence of $QR^X$ is independently Cl, Br, F, CN, $CF_3$, COOH, —N(CH$_3$)$_2$, —OH, CH$_2$OH, or an optionally substituted group selected from $C_{1-4}$alkoxy, $C_{1-4}$alkyl, phenyl, phenyloxy, benzyl, or benzyloxy.

37. The compound of claim 1, having one of the structures:

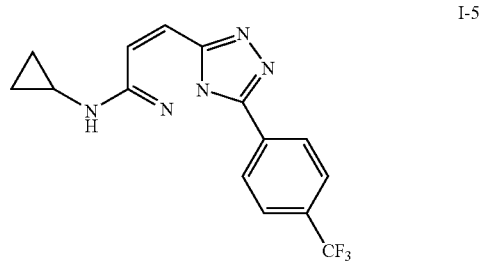

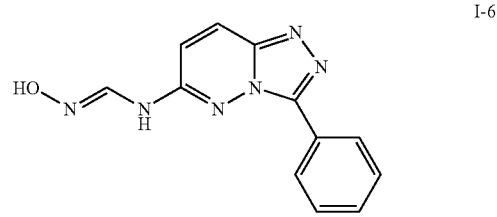

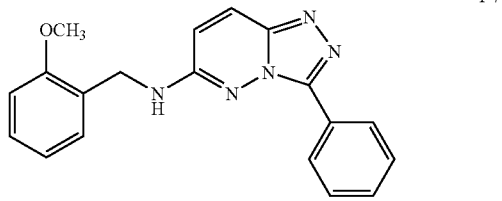

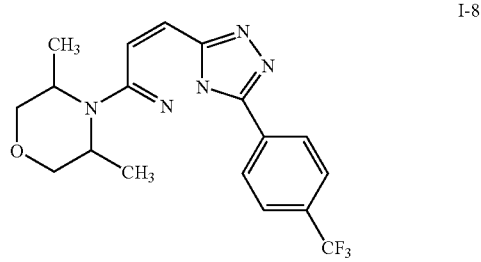

wherein x is 0-5, Q is a bond or is a $C_1$-$C_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of $R^X$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'; and wherein y is 0-5, Z is a bond or is a $C_1$-$C_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of $R^Y$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'.

31. The compound of claim 29 or 30, wherein y is 0-3 and $R^3$ is substituted with 0-3 occurrences of $ZR^Y$, and x is 0-3 and $R^2$ is substituted with 0-3 occurrences of $QR^X$.

32. The compound of claim 29 or 30, wherein y is 0, 1, or 2; and x is 0, 1, or 2.

-continued
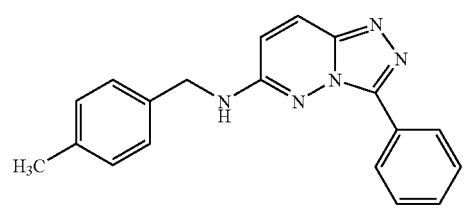
I-10
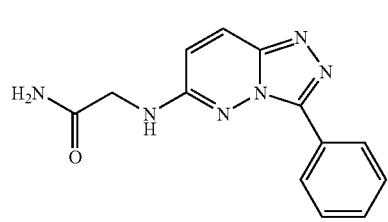
I-14
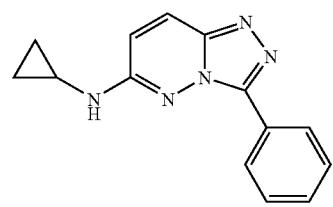
I-15
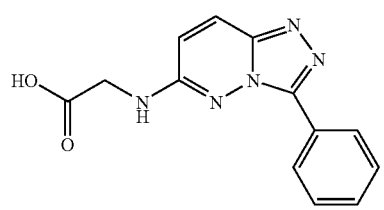
I-16
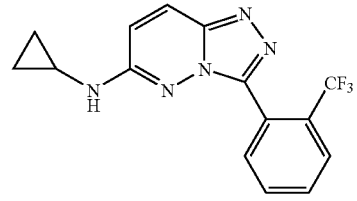
I-17
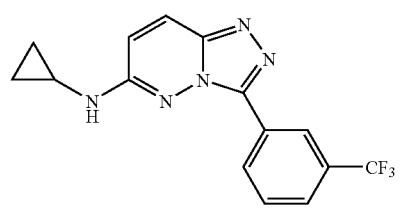
I-18
I-19
-continued
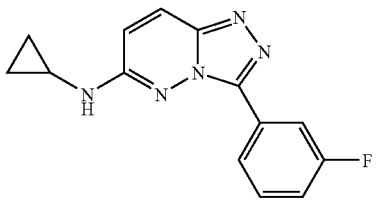
I-20
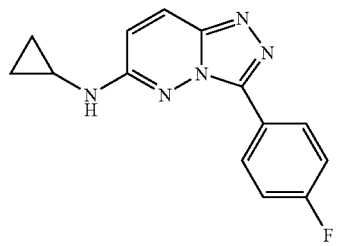
I-21
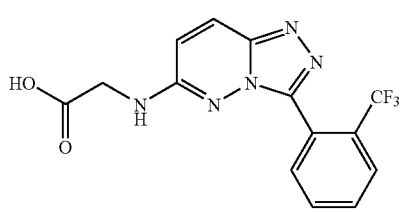
I-22
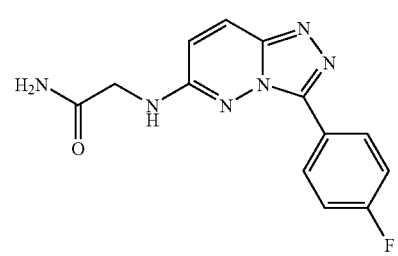
I-23
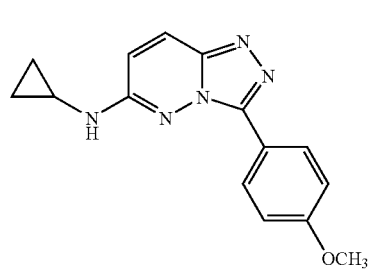
I-24
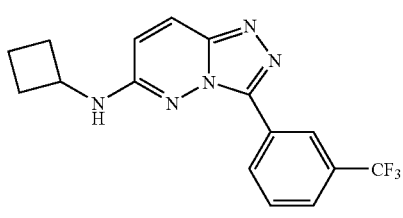
I-25
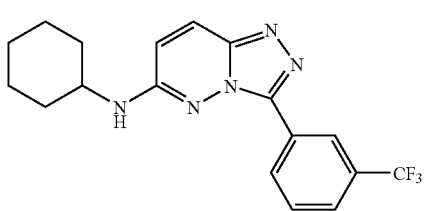
I-26

-continued
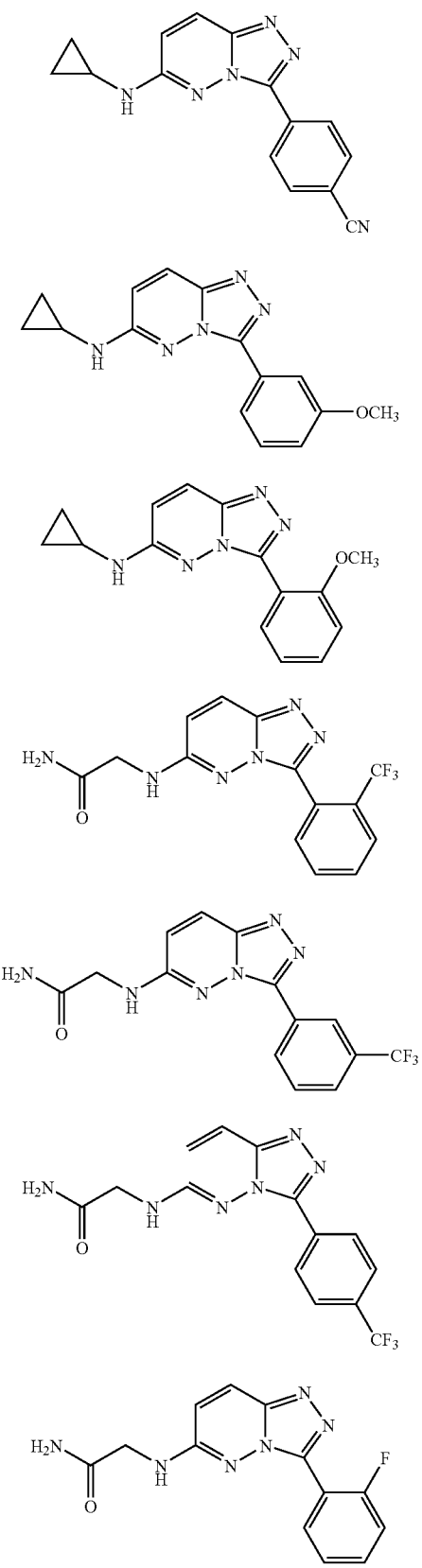
I-27
I-28
I-29
I-30
I-31
I-32
I-33
-continued
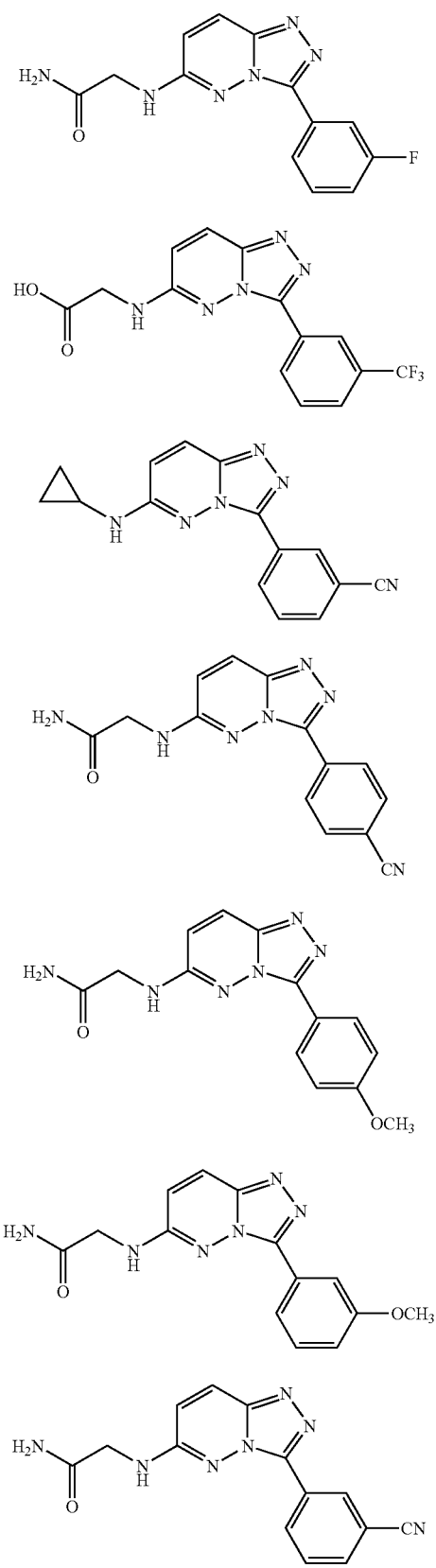
I-34
I-35
I-36
I-37
I-38
I-39
I-40

-continued
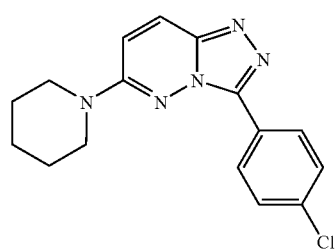
I-41
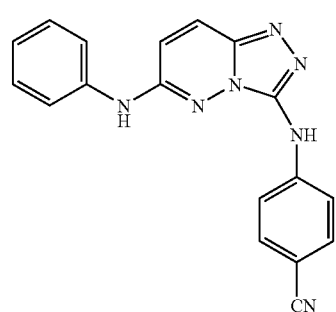
I-71
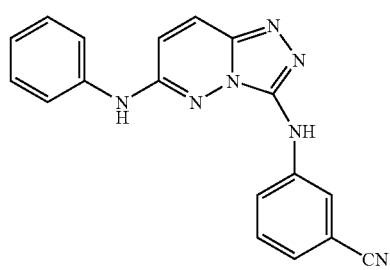
I-73
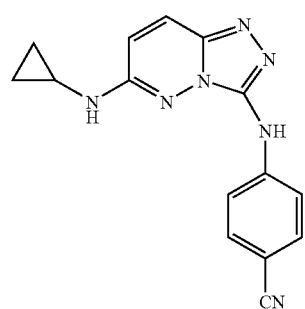
I-76
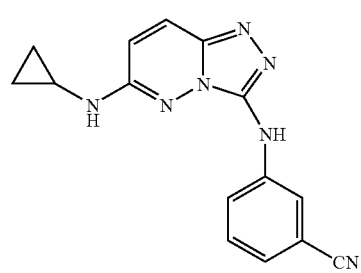
I-77
-continued
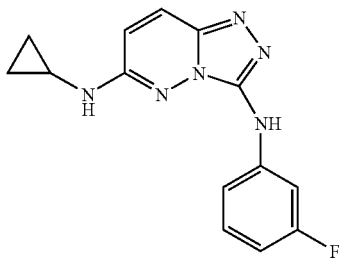
I-78
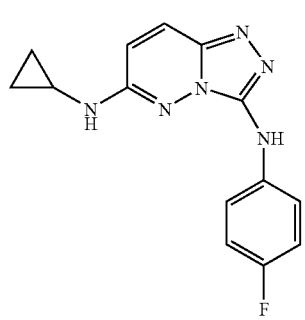
I-79
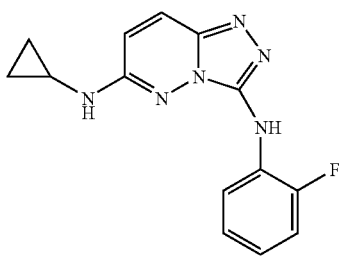
I-80
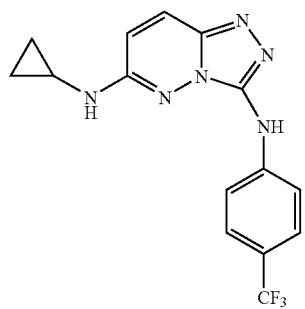
I-81
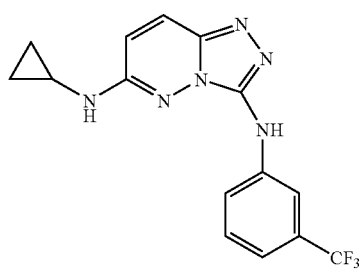
I-82

-continued

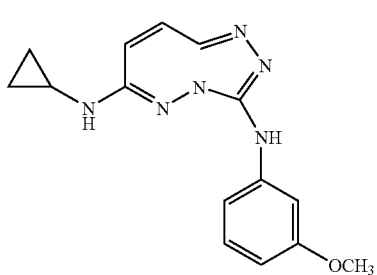
I-83

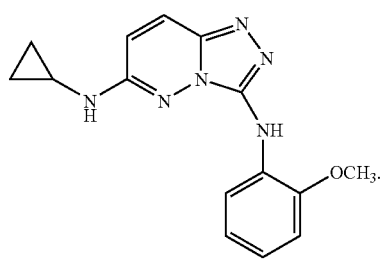
I-84

38. A composition comprising a compound having the formula:

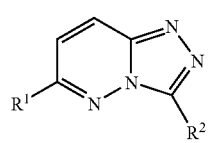
(I)

or a pharmaceutically acceptable salt thereof,
wherein $R^1$ is $NR^3R^4$; wherein $R^4$ is hydrogen or optionally substituted $C_{1-4}$alkyl and $R^3$ is an optionally substituted aryl, heteroaryl, cycloaliphatic, or heterocycloaliphatic group
each occurrence of R is independently selected from hydrogen or an optionally substituted $C_{1-6}$ aliphatic group, and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together, or two occurrences of R' on the same substituent or different substituents, taken together, form a 5-8 membered heterocyclyl or heteroaryl ring having 1-3 heteroatoms independently selected from nitrogen, oxygen, or sulfur; and
$R^2$ is $-(T)_nAr^1$, wherein T is NR; n is 0 or 1; $Ar^1$ is an optionally substituted group selected from

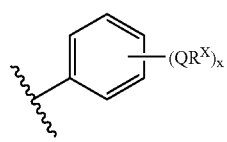
a

-continued

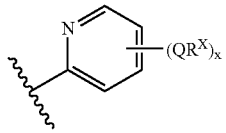
b

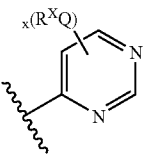
c

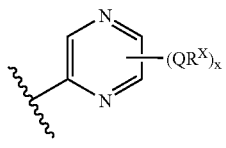
d

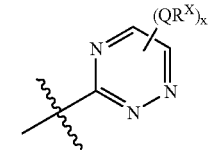
e

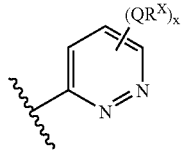
f

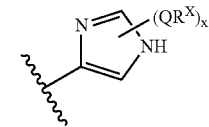
g

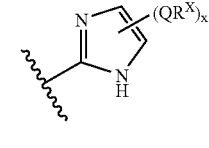
h

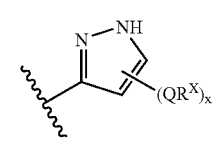
i

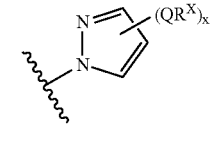
j

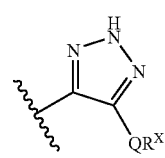
k

-continued
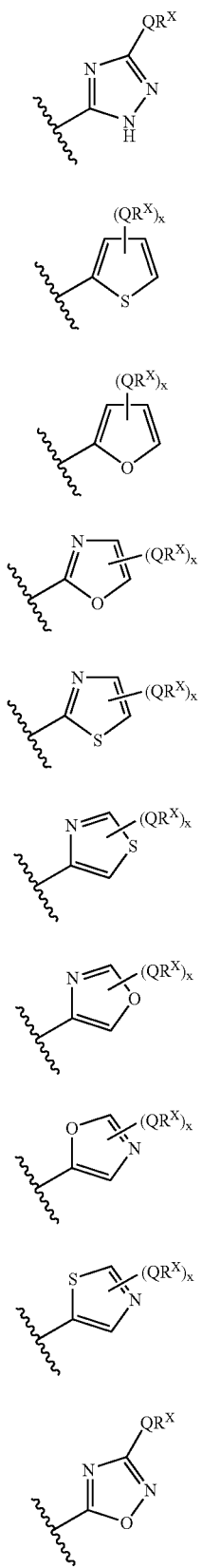
-continued
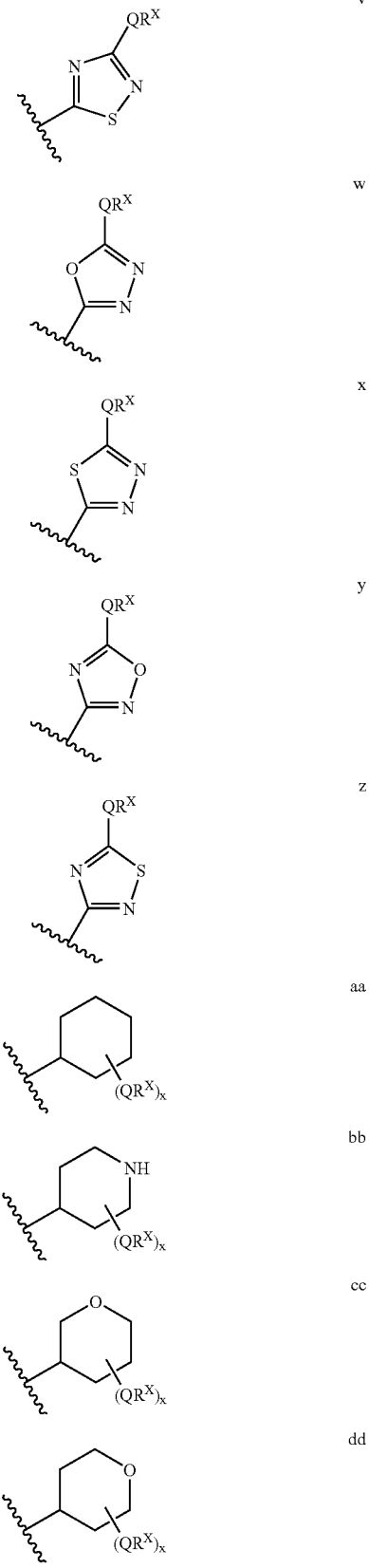

-continued

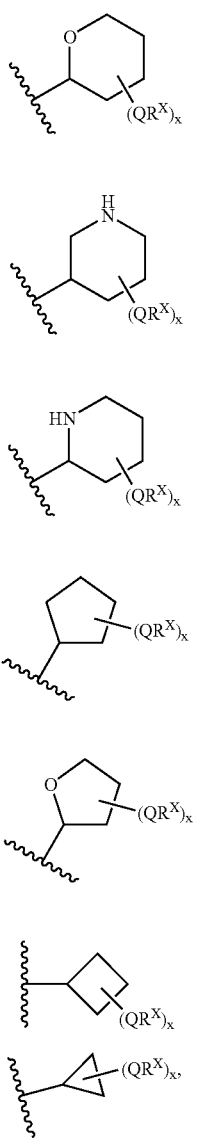

ee ff gg hh ii jj kk wherein any substitutable carbon or nitrogen atom is optionally substituted and wherein x is 0-5, Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, CN, OR', SR', N(R')$_2$, NR'C(O)R', NR'C(O)N(R')$_2$, $NR'CO_2R'$, C(O)R', $CO_2R'$, OC(O)R', C(O)N(R')$_2$, OC(O)N(R')$_2$, SOR', $SO_2R'$, $SO_2N(R')_2$, $NR'SO_2R'$, $NR'SO_2N(R')_2$, C(O)C(O)R', or C(O)CH$_2$C(O)R';

and a pharmaceutically acceptable carrier, adjuvant, or vehicle.

39. A method of inhibiting PIM-1, GSK-3, CDK-2, or SRC kinase activity in a biological sample selected from a cell culture, biopsied material obtained from a mammal, saliva, urine, feces, semen tears, or extracts thereof;

which method comprises contacting said biological sample with:

a) a composition of claim 38; or b) a compound having the structure:

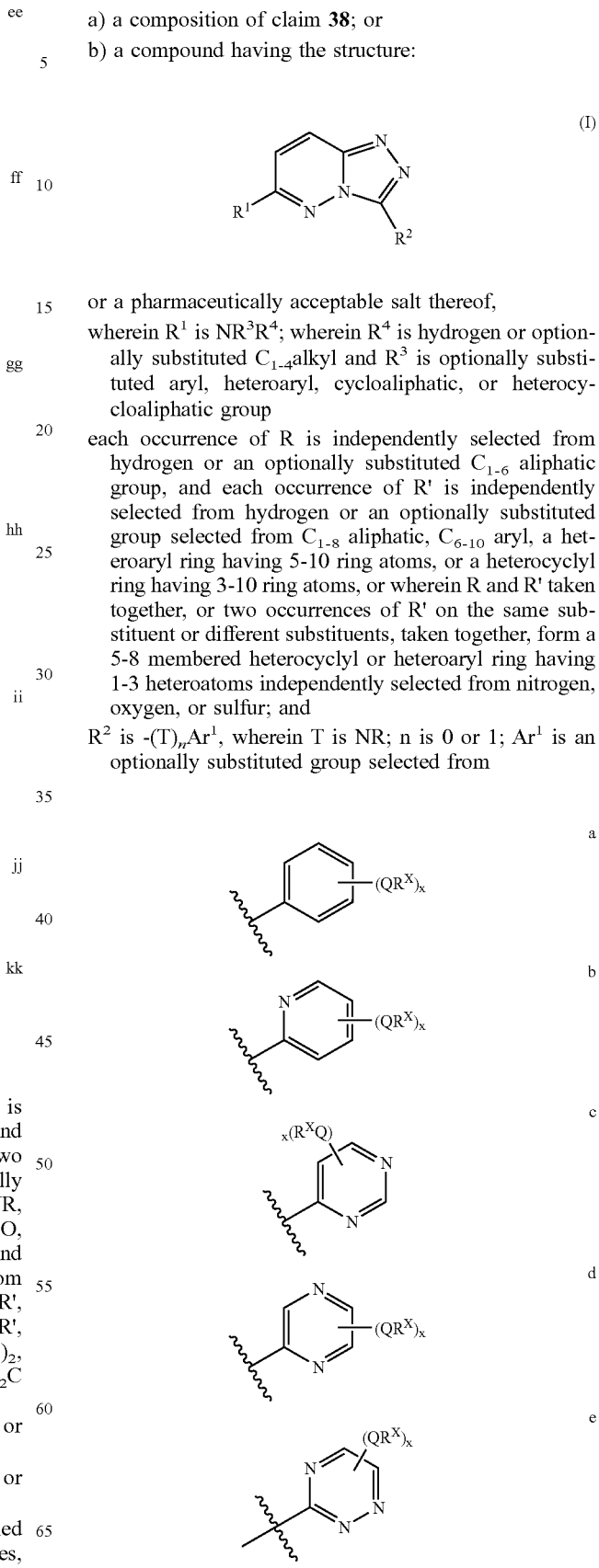

(I)

or a pharmaceutically acceptable salt thereof, wherein $R^1$ is $NR^3R^4$; wherein $R^4$ is hydrogen or optionally substituted $C_{1-4}$alkyl and $R^3$ is optionally substituted aryl, heteroaryl, cycloaliphatic, or heterocycloaliphatic group each occurrence of R is independently selected from hydrogen or an optionally substituted $C_{1-6}$ aliphatic group, and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together, or two occurrences of R' on the same substituent or different substituents, taken together, form a 5-8 membered heterocyclyl or heteroaryl ring having 1-3 heteroatoms independently selected from nitrogen, oxygen, or sulfur; and $R^2$ is -(T)$_n$Ar$^1$, wherein T is NR; n is 0 or 1; Ar$^1$ is an optionally substituted group selected from a b c d e

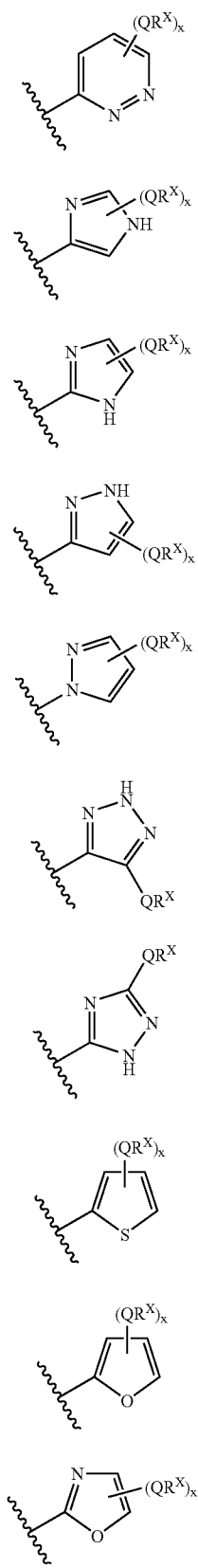
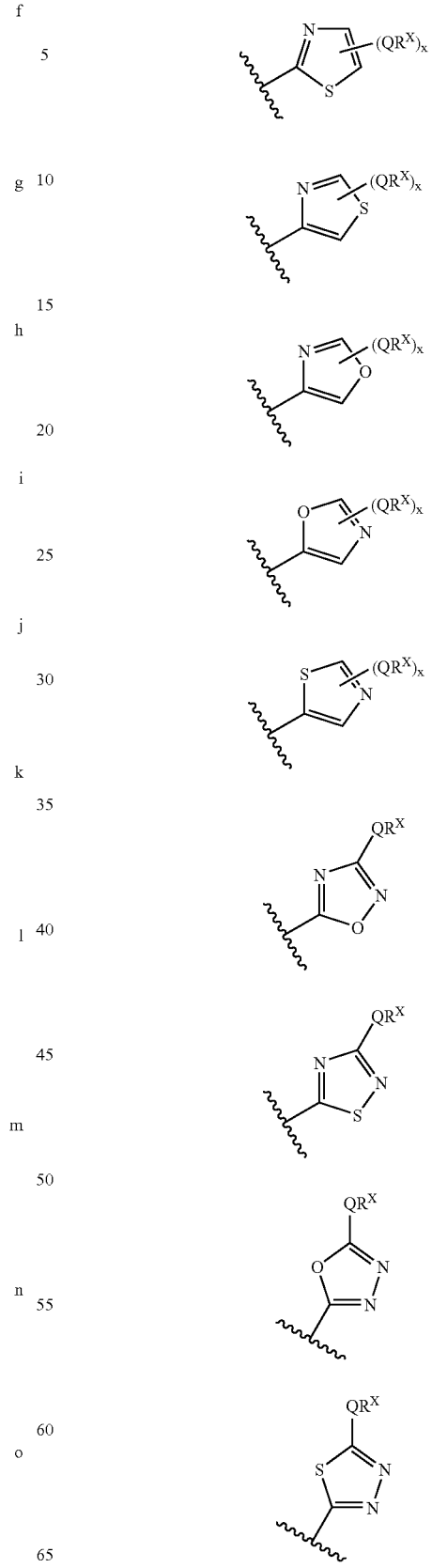

-continued y 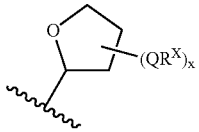

z 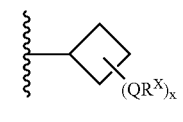

aa 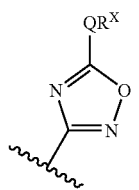

bb 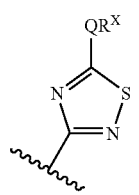

cc 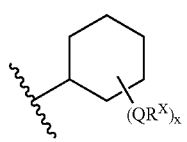

dd 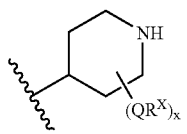

ee 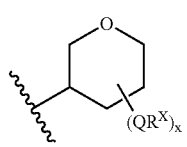

ff 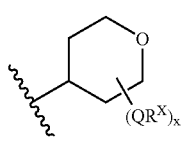

gg 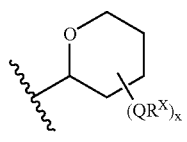

hh 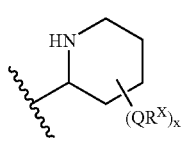

-continued ii 

jj kk 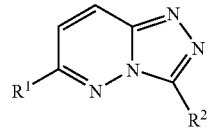

wherein any substitutable carbon or nitrogen atom is optionally substituted and wherein x is 0-5, Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, CN, OR', SR', N(R')$_2$, NR'C(O)R', NR'C(O)N(R')$_2$, $NR'CO_2R'$, C(O)R', $CO_2R'$, OC(O)R', C(O)N(R')$_2$, OC(O)N(R')$_2$, SOR', $SO_2R'$, $SO_2N(R')_2$, $NR'SO_2R'$, $NR'SO_2N(R')_2$, C(O)C(O)R', or $C(O)CH_2C(O)R'$.

40. The method of claim 39, wherein the method comprises inhibiting PIM-1 activity.

41. A method of treating or lessening the severity of a disease of condition selected from chronic myelogenous leukemia (CML), acute myeloid leukemia (AML), or acute promyelocytic leukemia (APL) comprising the step of administering to said patient:

a) a composition according to claim 38; or b) a compound having the structure:

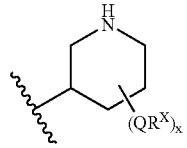

(I)

or a pharmaceutically acceptable salt thereof, wherein $R^1$ is $NR^3R^4$; wherein $R^4$ is hydrogen or optionally substituted $C_{1-4}$alkyl and $R^3$ is optionally substituted aryl, heteroaryl, cycloaliphatic, or heterocycloaliphatic group each occurrence of $R^2$ is independently selected from hydrogen or an optionally substituted $C_{1-6}$ aliphatic group, and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together, or two occurrences of R' on the same substituent or different substituents, taken together, form a 5-8 membered heterocyclyl or heteroaryl ring having 1-3 heteroatoms independently selected from nitrogen, oxygen, or sulfur; and $R^2$ is -$(T)_n Ar^1$, wherein T is NR; n is 0 or 1; $Ar^1$ is an optionally substituted group selected from
a
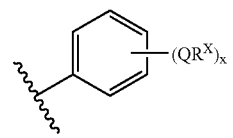
b
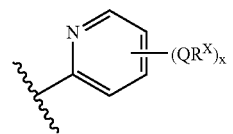
c
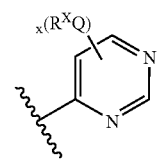
d
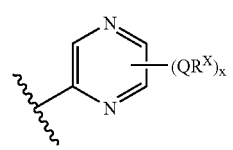
e
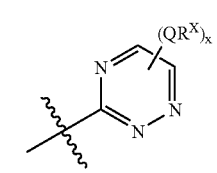
f
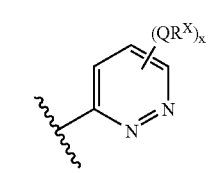
g
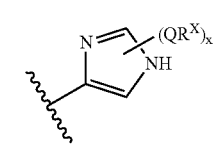
h
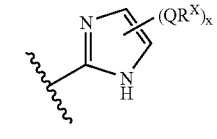
i
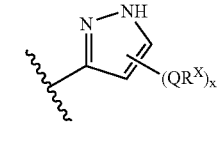
j
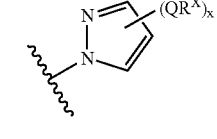
-continued
k
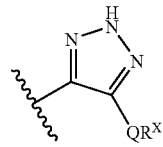
l
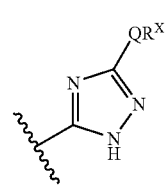
m
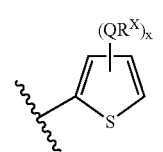
n
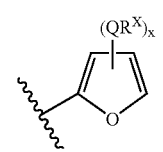
o
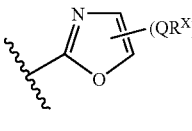
p
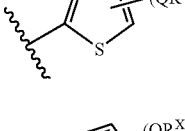
q
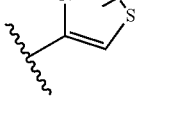
r
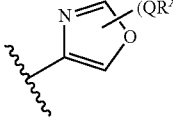
s
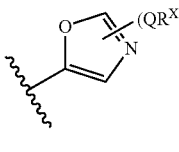
t
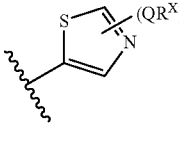

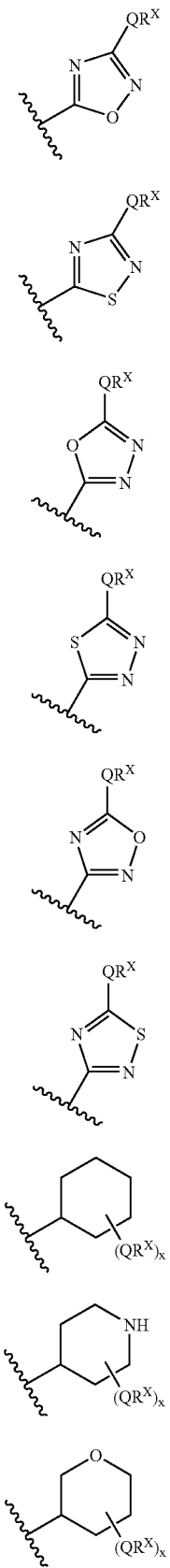

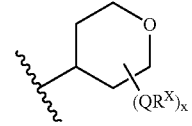
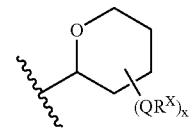
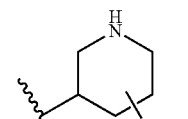
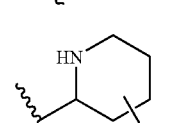
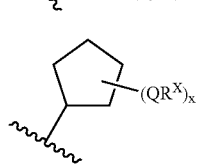
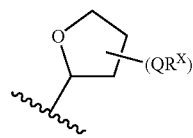
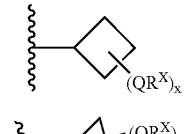
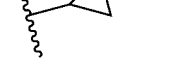

wherein any substitutable carbon or nitrogen atom is optionally substituted and wherein x is 0-5, Q is a bond or is a $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'.

42. The method according to claim 41, comprising the additional step of administering to said patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders, wherein:

said additional therapeutic agent is appropriate for the disease being treated; and said additional therapeutic agent is administered together with said composition as a single dosage form or separately from said composition as part of a multiple dosage form.

* * * * *